(12) United States Patent
Koga et al.

(10) Patent No.: US 9,097,681 B2
(45) Date of Patent: Aug. 4, 2015

(54) INSPECTION DEVICE, BONDING SYSTEM AND INSPECTION METHOD

(71) Applicant: TOKYO ELECTRON LIMITED, Tokyo (JP)

(72) Inventors: Shinji Koga, Koshi (JP); Akinori Miyahara, Koshi (JP); Hiroshi Tomita, Koshi (JP); Shuji Iwanaga, Koshi (JP); Takeshi Tamura, Koshi (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 97 days.

(21) Appl. No.: 13/967,896

(22) Filed: Aug. 15, 2013

(65) Prior Publication Data

US 2014/0054463 A1    Feb. 27, 2014

(30) Foreign Application Priority Data

Aug. 23, 2012   (JP) .................................. 2012-184086

(51) Int. Cl.
| | |
|---|---|
| *G01B 11/00* | (2006.01) |
| *G01B 11/02* | (2006.01) |
| *G01N 21/84* | (2006.01) |
| *G01N 21/95* | (2006.01) |
| *H01L 21/66* | (2006.01) |

(52) U.S. Cl.
CPC ................ *G01N 21/84* (2013.01); *G01B 11/00* (2013.01); *G01B 11/028* (2013.01); *G01N 21/9505* (2013.01); *H01L 22/12* (2013.01); *H01L 2924/0002* (2013.01)

(58) Field of Classification Search
CPC ...... G01B 11/00; G01B 11/028; G01N 21/84; G01N 21/9503
See application file for complete search history.

(56) References Cited

U.S. PATENT DOCUMENTS

| | | | |
|---|---|---|---|
| 2002/0174958 A1* | 11/2002 | Yanagita et al. ............... | 156/584 |
| 2003/0003608 A1* | 1/2003 | Arikado et al. ................. | 438/14 |
| 2006/0068682 A1* | 3/2006 | Rodriguez et al. ............. | 451/5 |
| 2009/0073445 A1* | 3/2009 | Kobayashi .................... | 356/394 |
| 2009/0196489 A1* | 8/2009 | Le ................................. | 382/148 |

FOREIGN PATENT DOCUMENTS

| | | |
|---|---|---|
| JP | 5-302885 A | 11/1993 |
| JP | 2002-050749 A | 2/2002 |
| JP | 2006-269915 A | 10/2006 |
| JP | 2011-066283 A | 3/2011 |
| JP | 2011-187716 A | 9/2011 |

* cited by examiner

*Primary Examiner* — David Porta
*Assistant Examiner* — Mindy Vu
(74) *Attorney, Agent, or Firm* — Nath, Goldberg & Meyer; Jerald L. Meyer

(57) ABSTRACT

According to an embodiment of the present disclosure, an apparatus of inspecting an overlapped substrate obtained by bonding substrates together is provided. The apparatus includes a first holding unit configured to hold and rotate the overlapped substrate, and a displacement gauge configured to measure displacements of peripheral sides of a first substrate and a second substrate constituting the overlapped substrate while rotating the overlapped substrate held by the first holding unit.

9 Claims, 30 Drawing Sheets

INSPECTION DEVICE, BONDING SYSTEM AND INSPECTION METHOD

CROSS-REFERENCE TO RELATED APPLICATION

This application claims the benefit of Japanese Patent Application No. 2012-184086, filed on Aug. 23, 2012, in the Japan Patent Office, the disclosure of which is incorporated herein in its entirety by reference.

TECHNICAL FIELD

The present disclosure relates to an inspection device which inspects an overlapped substrate formed by bonding substrates together, a bonding system including the inspection device and an inspection method using the inspection device.

BACKGROUND

In recent years, high integration of semiconductor devices has been prompted. Meanwhile, when a plurality of highly-integrated semiconductor devices is arranged on a horizontal plane and is connected by wires for production, an increase in a wire length increases wire resistance and a wire delay.

To overcome this problem, the use of a three-dimensional integration technique has been proposed which stacks semiconductor devices in three dimensions. In the three-dimensional integration technique, for example, a bonding system is used to bond two semiconductor wafers (hereinafter, simply referred to as "wafers") together. For example, the bonding system includes a surface hydrophilization device, which hydrophilizes bonding surfaces of substrates, and a bonding device which bonds the substrates whose surfaces are hydrophilized by the surface hydrophilization device. In the bonding system, the surface hydrophilization device supplies pure water onto the surfaces of the substrates to hydrophilize the surfaces, and subsequently, the bonding device bonds the substrates together by virtue of the Van der Waals force and a hydrogen bonding (intermolecular force).

Stably bonding the two wafers requires preventing a misalignment between relative positions of the two wafers to be bonded. Typically, an inspection operation for a bonding state of the wafers has been performed by, e.g., moving an image pickup camera in horizontal and vertical directions and measuring reference points formed on the wafers by the image pickup camera. Unfortunately, a conventional inspection device used in this inspection operation requires a triaxial moving equipment, which causes an increase in the size of the inspection device.

SUMMARY

Some embodiments of the present disclosure provide an inspection device, a bonding system including the inspection device and an inspection method using the inspection device, which are capable of miniaturizing the inspection device configured to inspect an overlapped substrate obtained by bonding substrates together and capable of stably inspecting a bonding state of the overlapped substrate.

According to an embodiment of the present disclosure, an apparatus of inspecting an overlapped substrate obtained by bonding substrates together is provided. The apparatus includes a first holding unit configured to hold and rotate the overlapped substrate, and a displacement gauge configured to measure displacements of peripheral sides of a first substrate and a second substrate constituting the overlapped substrate while rotating the overlapped substrate held by the first holding unit.

According to another embodiment of the present disclosure, there is provided a bonding system including the inspection device comprising includes a first holding unit configured to hold and rotate the overlapped substrate, and a displacement gauge configured to measure displacements of peripheral sides of a first substrate and a second substrate constituting the overlapped substrate while rotating the overlapped substrate held by the first holding unit. The bonding system includes a processing station including a plurality of processing units configured to perform a predetermined process to bond substrates together, and a substrate transfer zone in which first and second substrates before the bonding or an overlapped substrate after the bonding are transferred to the plurality of processing units, and a carry-in/carry-out station in which the first and second substrates before the bonding or the overlapped substrate after the bonding are carried in and out the processing station. In the boding system, the inspection device is disposed adjacent to the substrate transfer zone and the carry-in/carry-out station inside the processing station.

According to a still another embodiment of the present disclosure, there is provided a method of inspecting an overlapped substrate obtained by bonding substrates together using an inspection device. The inspection device includes a first holding unit configured to hold and rotate the overlapped substrate, and a displacement gauge configured to measure a displacement of a peripheral side of the overlapped substrate held by the first holding unit. The inspection method includes measuring, by the displacement gauge, displacements of peripheral sides of first and second substrates constituting the overlapped substrate while rotating the overlapped substrate held by the first holding unit, and inspecting a bonding state of the overlapped substrate.

BRIEF DESCRIPTION OF THE DRAWINGS

The accompanying drawings, which are incorporated in and constitute a part of the specification, illustrate embodiments of the present disclosure, and together with the general description given above and the detailed description of the embodiments given below, serve to explain the principles of the present disclosure.

DETAILED DESCRIPTION

Reference will now be made in detail to various embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, systems, and components have not been described in detail so as not to unnecessarily obscure aspects of the various embodiments.

Figure 1:
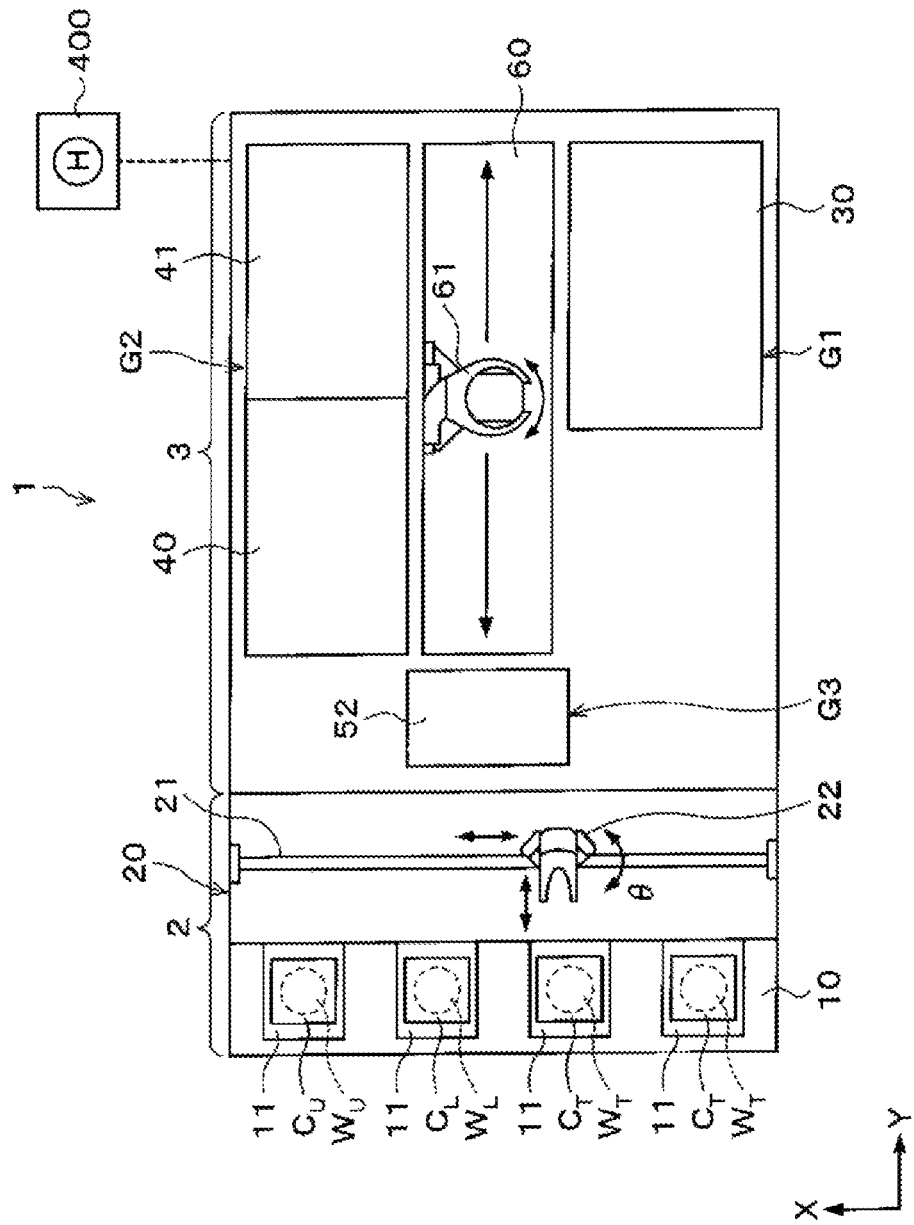
FIG. 1 is a schematic plane view showing a configuration of a bonding system according to one embodiment.
Figure 2:
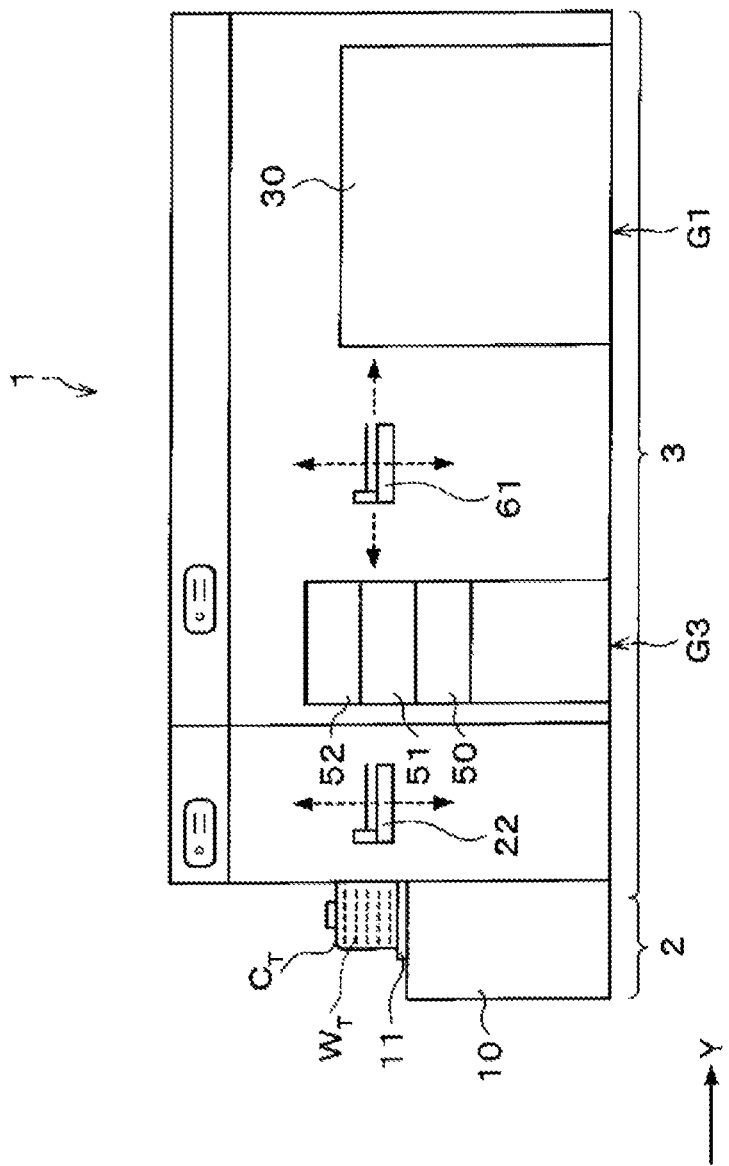
FIG. 2 is a schematic side view showing an internal configuration of the bonding system according to one embodiment.

FIG. 1 is a schematic plane view showing a configuration of a bonding system 1 according to one embodiment. FIG. 2 is a schematic side view showing an internal configuration of the bonding system 1.

Figure 3:
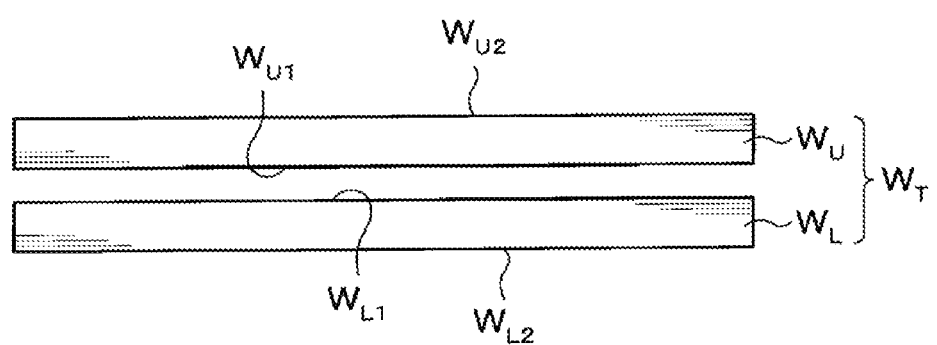
FIG. 3 is a schematic side view showing configurations of an upper wafer and a lower wafer.

In the bonding system 1, for example, wafers $W_U$ and $W_L$ as two substrates are bonded together as shown in FIG. 3. In the following description, a wafer placed on the upper side will be referred to as an "upper wafer $W_U$" as a first substrate, and a wafer placed on the lower side will be referred to as a "lower wafer $W_L$" as a second substrate. In the upper wafer $W_U$, a surface that is bonded to the lower wafer $W_L$ will be referred to as a "front surface $W_{U1}$", and an opposite surface of the front surface $W_{U1}$ will be referred to as a "rear surface $W_{U2}$." Similarly, in the lower wafer $W_L$, a surface that is bonded to the upper wafer $W_U$ will be referred to as a "front surface $W_{L1}$" and an opposite surface of the front surface $W_{L1}$ will be referred to as a "rear surface $W_{L2}$". Further, in the bonding system 1, an overlapped wafer $W_T$ as an overlapped substrate is obtained by bonding the upper wafer $W_U$ and the lower wafer $W_L$ together.

As shown in FIG. 1, the bonding system 1 includes a carry-in/carry-out station 2 in which cassettes $C_U$, $C_L$, and $C_T$ are carried in and out between the carry-in/carry-out station 2 and the outside, and a processing station 3 including various processing units which are configured to perform a predetermined process on the wafers $W_U$, $W_L$ and $W_T$, in which the carry-in/carry-out station 2 and the processing station 3 are connected serially. The cassettes $C_U$, $C_L$, and $C_T$ are configured to accommodate a plurality of wafers $W_U$ and $W_L$, and a plurality of overlapped wafers $W_T$ therein, respectively.

A cassette loading table 10 is disposed in the carry-in/carry-out station 2. A plurality of (e.g., four) cassette loading boards 11 are installed on the cassette loading table 10. The cassette loading boards 11 are arranged in a line along an X-axis direction (vertical direction in FIG. 1). The cassette loading boards 11 can load thereon the cassettes $C_U$, $C_L$ and $C_T$, when they are carried in and out between the carry-in/carry-out station 2 and the outside of the bonding system 1, respectively. In this way, the carry-in/carry-out station 2 can hold the plurality of upper wafers $W_U$, the plurality of lower wafers $W_L$ and the plurality of overlapped wafers $W_T$. The number of the cassette loading boards 11 is not limited to this embodiment but may be selected as appropriate. One of the cassettes may be used as a collection cassette for collecting defective wafers. That is, the collection cassette is provided to receive the defective wafers having a defect due to various factors in the bonding of the upper wafer $W_U$ and the lower wafer $W_L$, except normal overlapped wafers $W_T$. In this embodiment, one of the plurality of cassettes $C_T$ is used as the collection cassette for collecting the defective wafers and the other cassettes $C_T$ are used to receive the normal overlapped wafers $W_T$.

In the carry-in/carry-out station 2, a wafer transfer section 20 is disposed adjacent to the cassette loading table 10. The wafer transfer section 20 is provided with a wafer transfer unit 22 configured to move along a transfer path 21 extending in the X-axis direction. The wafer transfer unit 22, which is movable in a vertical direction and is also rotatable around a vertical axis (or in θ direction), transfers the wafer $W_U$, the wafer $W_L$ and the overlapped wafer $W_T$ between the cassettes $C_U$, $C_L$ and $C_T$ loaded on the respective cassette loading boards 11, and an inspection device 50, transition units 51 and 52 of a third processing block G3 of the processing station 3, which will be described later with reference to FIG. 2.

The processing station 3 is provided with a plurality of (e.g., three) processing blocks G1, G2 and G3 which include various processing units. For example, the first processing block G1 is disposed at the front side of the processing station 3 along the X-axis direction (at the lower side in FIG. 1). The second processing block G2 is disposed at the back side of the processing station 3 in the X-axis direction (at the upper side in FIG. 1). The third processing block G3 is disposed in the vicinity of the carry-in/carry-out station 2 (at the backside of the processing station 3 in a Y-axis direction in FIG. 1).

The first processing block G1 is provided with a surface modification device 30 configured to modify the front surfaces $W_{U1}$ and $W_{L1}$ of the wafers $W_U$ and $W_L$. In this embodiment, the surface modification device 30 cuts a $SiO_2$ bonding in the front surfaces $W_{U1}$ and $W_{L1}$ of the wafers $W_U$ and $W_L$ to obtain a single-bonding SiO, and then modifies the front surfaces $W_{U1}$ and $W_{L1}$ of the wafers $W_U$ and $W_L$ so that they can be easily hydrophilized.

The second processing block G2 is provided with a surface hydrophilization device 40 configured to hydrophilize and clean the front surfaces $W_{U1}$ and $W_{L1}$ of the wafers $W_U$ and $W_L$ with, e.g., pure water, and a bonding device 41 configured to bond the wafers $W_U$ and $W_L$ together, which are arranged from the carry-in/carry-out station 2 in the Y-axis direction in that order from the bottom.

The third processing block G3 is provided with the inspection device 50 configured to inspect the interior of the overlapped wafer $W_T$, and the transition units 51 and 52 configured to transit the wafers $W_U$ and $W_L$ and the overlapped wafer $W_T$, which are stacked in three stages in order from the bottom, as shown in FIG. 2.

As shown in FIG. 1, an area which is bounded by the first to third processing blocks G1 to G3 is defined as a wafer transfer zone 60, which serves as a substrate transfer zone. For example, a wafer transfer unit 61 is disposed in the wafer transfer zone 60.

The wafer transfer unit 61 is equipped with a transfer arm (not shown) which is movable in a vertical direction, horizontal directions (the X and Y-axis directions) and is rotatable around a vertical axis. The wafer transfer unit 61 moves inside the wafer transfer zone 60 so that the wafers $W_U$ and $W_L$ and the overlapped wafer $W_T$ are transferred to a respective processing unit installed in each of the first to third processing blocks G1, G2 and G3.

Figure 4:
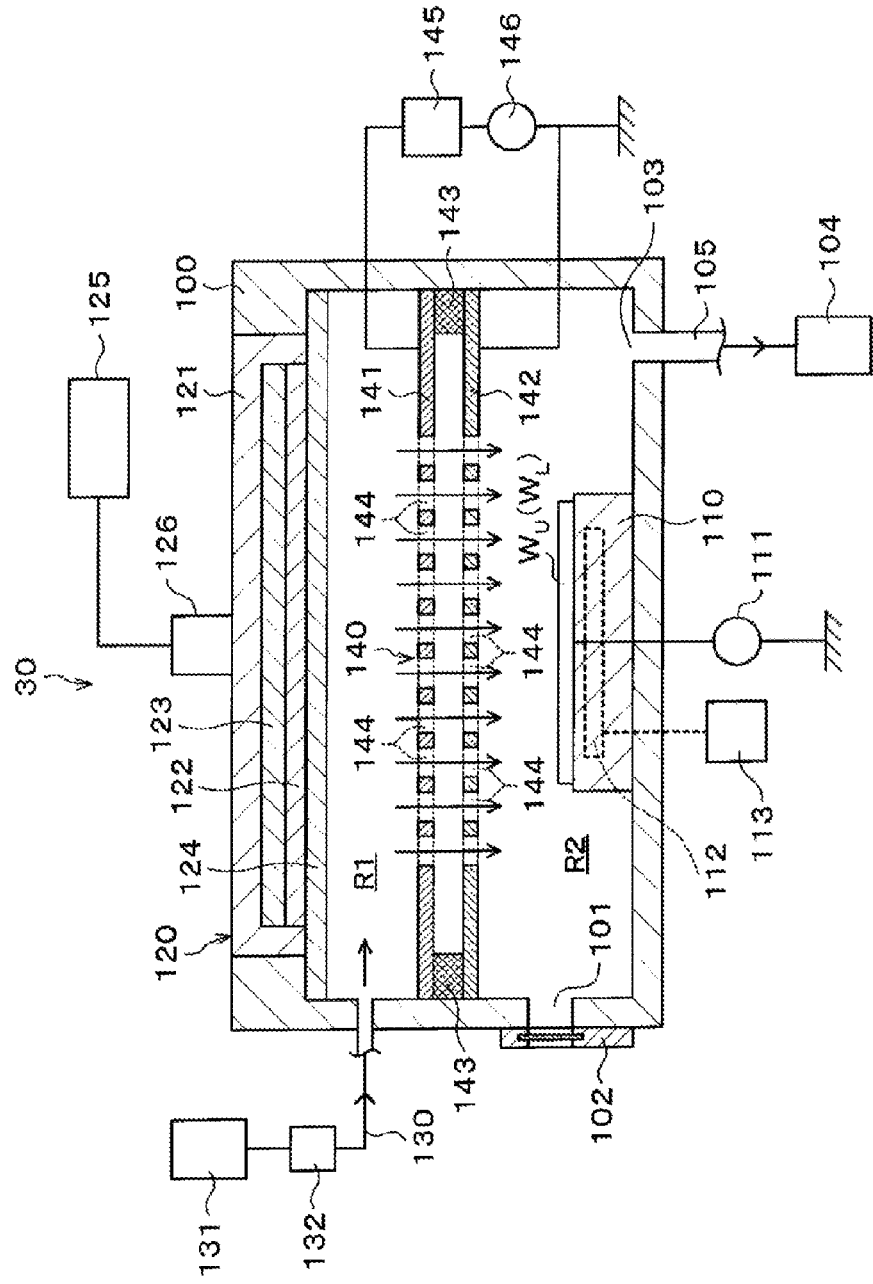
FIG. 4 is a longitudinal sectional view schematically showing a configuration of a surface modification device.

Next, a configuration of the abovementioned surface modification device 30 will be described. As shown in FIG. 4, the surface modification device 30 includes a processing vessel 100. The processing vessel 100 includes an opened upper portion at which a radial line slot antenna 120 (which will be described later) is disposed such that the processing vessel 100 is internally sealed.

An inlet/outlet 101 through which the wafers $W_U$ and $W_L$ are carried in and out is formed in a lateral side facing the wafer transfer zone 60 in the processing vessel 100, and a gate valve 102 is installed in the inlet/outlet 101.

An air suction hole 103 is formed at the bottom surface of the processing vessel 100. The air suction hole 103 is connected with an air suction pipe 105 communicating with an air suction unit 104 which reduces an internal atmosphere of the processing vessel 100 to a predetermined degree of vacuum.

A loading table 110 on which the wafer $W_U$ (or $W_L$) is loaded is disposed on the bottom surface of the processing vessel 100. The loading table 110 can load the wafer $W_U$ (or $W_L$) thereon by virtue of, e.g., an electrostatic absorption or a vacuum absorption. An ion ampere meter 111 configured to measure an ion current generated by ions (oxygen ions) of a process gas, which are radiated onto the wafer $W_U$ (or $W_L$) loaded on the loading table 110, is disposed in the loading table 110, as will be described later.

The loading table 110 includes a temperature control mechanism 112 configured to circulate, e.g., a cooling medium. The temperature control mechanism 112 is connected to a liquid temperature control unit 113 configured to control a temperature of the cooling medium. The liquid temperature control unit 113 controls the temperature of the cooling medium to control the temperature of the loading table 110. This configuration maintains the wafer $W_U$ (or $W_L$) loaded on the loading table 110 at a predetermined temperature.

Elevating pins (not shown), which elevate the wafers $W_U$ and $W_L$ supported from the bottom are disposed below the loading table 110. The elevating pins are inserted through through-holes (not shown) formed in the loading table 110, respectively, in such a manner that they project from the top of the loading table 110.

The radial line slot antenna (RLSA) 120 configured to supply a microwave for plasma generation is disposed at the opened upper portion of the processing vessel 100. The radial line slot antenna 120 includes an antenna body 121 with an opened bottom portion. For example, a flow path (not shown) through which the cooling medium flows is formed within the antenna body 121.

A slot plate 122 with a plurality of slots formed therein, which acts as an antenna, is disposed in the opened bottom portion of the antenna body 121. A conductive material such as copper, aluminum, nickel or the like, may be used as a material of the slot plate 122. A phase delay plate 123 is formed between the antenna body 121 and the slot plate 122. The phase delay plate 123 may be made of a low loss dielectric material such as quartz, alumina, aluminum nitride or the like.

A microwave transmitting plate 124 is disposed below the antenna body 121 and the slot plate 122. The microwave transmitting plate 124 is disposed to seal the processing vessel 100 through a seal member (not shown) such as an O-ring or the like. Examples of a material of the microwave transmitting plate 124 may include a dielectric such as quartz, $Al_2O_3$ or the like.

The top portion of the antenna body 121 is connected to a coaxial waveguide 126 which is connected to a microwave oscillator 125. The microwave oscillator 125 is provided at the outside of the processing vessel 100 and is configured to oscillate a microwave having a predetermined frequency, for example, 2.5 GHz, to the radial line slot antenna 120.

With this configuration, the microwave oscillated from the microwave oscillator 125 propagates through the radial line slot antenna 120, followed by being compressed into a wave of a short wavelength at the phase delay plate 123, followed by being converted the same into a circular polarized wave at the slot plate 122, followed by transmitting the microwave transmitting plate 124, so that the microwave is incident into the processing vessel 100.

A gas supply pipe 130 which supplies oxygen gas as the process gas into the processing vessel 100 is connected to the lateral side of the processing vessel 100. The gas supply pipe 130 is disposed above an ion conduction structure 140 (which will be described later) and supplies the oxygen gas into a plasma generation region R1 in the processing vessel 100. The gas supply pipe 130 is in communication with a gas source 131 to store the oxygen gas therein via a gas supply kit 132. The gas supply pipe 130 is connected to the gas supply kit 132 including a valve, a flow rate controller and the like, which is configured to control a flow of the oxygen gas.

The ion conduction structure 140 is disposed between the loading table 110 and the radial line slot antenna 120 in the processing vessel 100. Specifically, the ion conduction structure 140 is disposed to partition the interior of the processing vessel 100 into the plasma generation region R1 and a processing region R2. In the plasma generation region R1, the oxygen gas supplied through the gas supply pipe 130 is plasmarized by the microwave supplied from the radial line slot antenna 120. Further, in the processing region R2, the front surface $W_{U1}$ (or $W_{L1}$) of the wafer $W_U$ (or $W_L$) loaded on the loading table 110 is modified using oxygen ions generated in the plasma generation region R1.

The ion conduction structure 140 includes a pair of electrodes 141 and 142. In the following description, an electrode disposed at the upper side will be sometimes referred to as an upper electrode 141 and an electrode disposed at the lower side will be sometimes referred to as a lower electrode 142. An insulating member 143 is disposed between the pair of electrodes 141 and 142 to electrically insulate therebetween.

Figure 5:
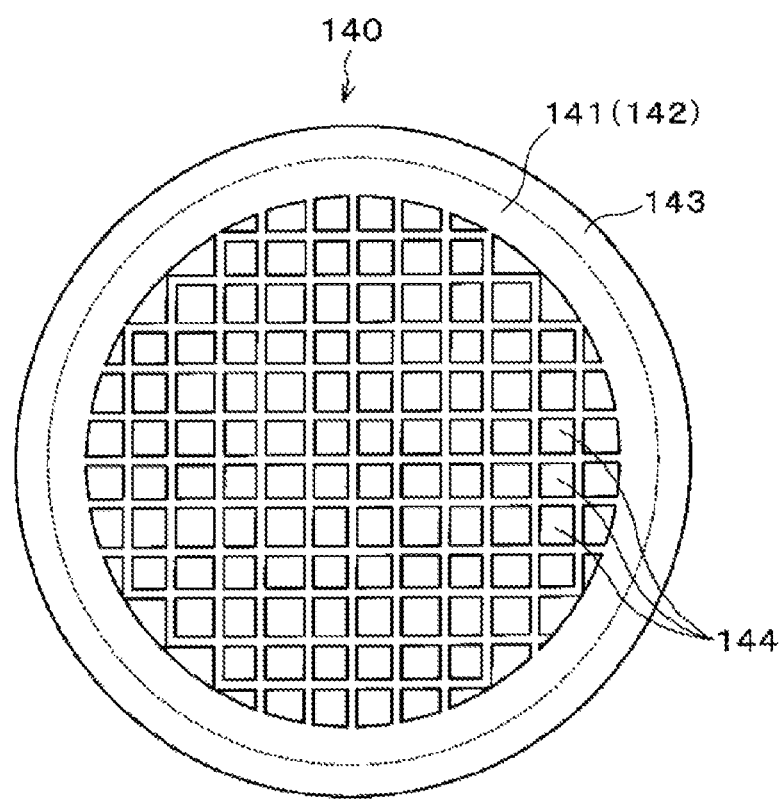
FIG. 5 is a plane view of an ion conduction structure.

As shown in FIGS. 4 and 5, each of the electrodes 141 and 142 is formed in a circular shape having a diameter larger than that of the wafer $W_U$ (or $W_L$) when viewed from the top. In addition, a plurality of openings 144 through which the oxygen ions are transferred from the plasma generation region R1 into the processing region R2, are formed in each of the electrodes 141 and 142. These openings 144 are arranged in, e.g., a grid pattern. The pattern or arrangement of the openings 144 are not limited to this embodiment but may be selected as appropriate.

In some embodiments, the dimension of each of the openings 144 may be set to be shorter than a wavelength of the microwave supplied from the radial line slot antenna 120. This allows the microwave supplied from the radial line slot antenna 120 to be reflected at the ion conduction structure 140, thereby preventing the microwave from introducing into the processing region R2. This prevents the wafer $W_U$ (or $W_L$) loaded on the loading table 110 from being directly exposed to the microwave, which makes it possible to prevent the wafer $W_U$ (or $W_L$) from being damaged by the microwave.

A power supply 145 is connected to the ion conduction structure 140 to apply a predetermined voltage across the pair of electrodes 141 and 142. The predetermined voltage applied from the power supply 145 is controlled by a controller 400 (see FIG. 1), which will be described later. As an example, the maximum value of the predetermined voltage may be 1 KeV.

In addition, the ion conduction structure 140 is connected to an ampere meter 146 which is configured to measure current flowing between the pair of electrodes 141 and 142.

Figure 6:
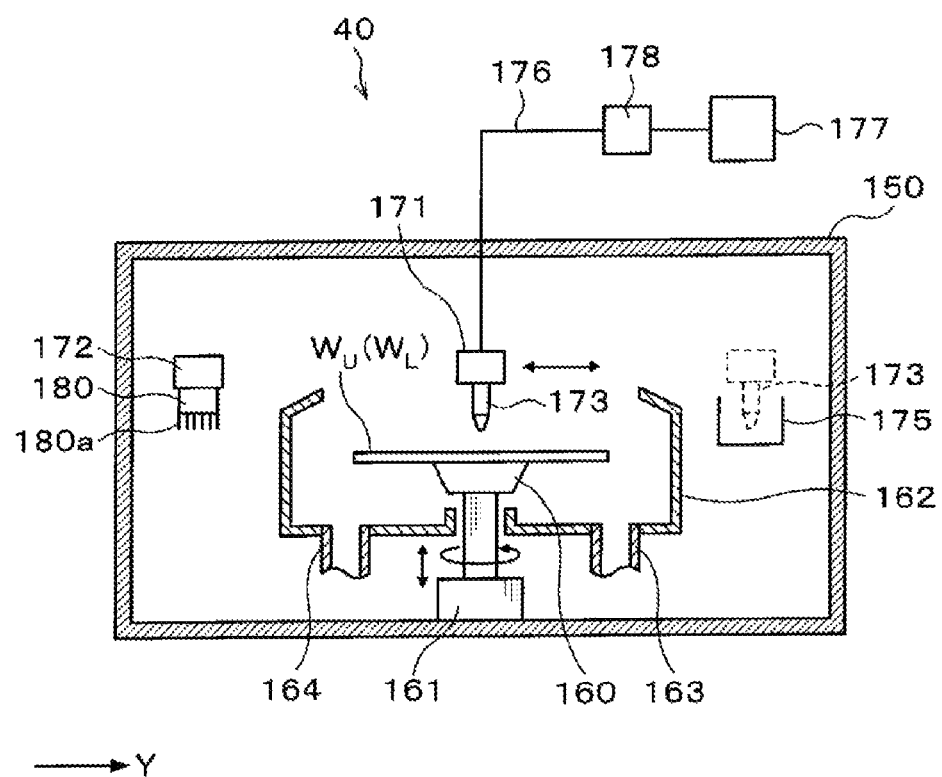
FIG. 6 is a longitudinal sectional view schematically showing a configuration of a surface hydrophilization device.
Figure 7:
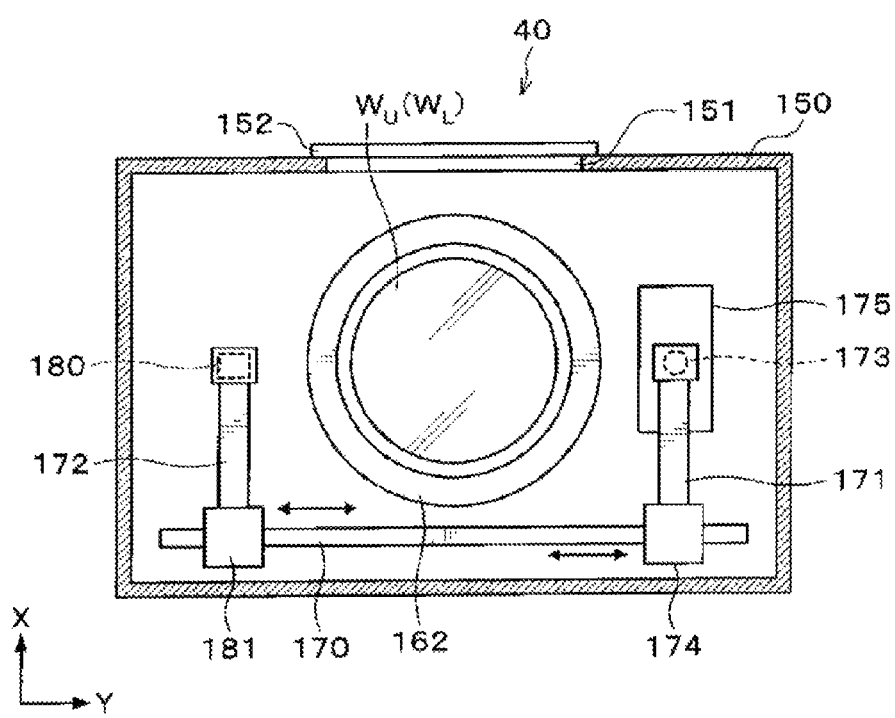
FIG. 7 is a traverse sectional view schematically showing the configuration of the surface hydrophilization device.

Next, a configuration of the surface hydrophilization device 40 will be described. As shown in FIG. 6, the surface hydrophilization device 40 includes an internally-sealable processing vessel 150. As shown in FIG. 7, An inlet/outlet 151 through which the wafer $W_U$ (or $W_L$) is carried in and out is formed at a lateral side facing the wafer transfer zone 60 in the processing vessel 150, and an opening/closing shutter 152 is disposed in the inlet/outlet 151.

As shown in FIG. 6, a spin chuck 160 configured to hold and rotate the wafer $W_U$ (or $W_L$) is disposed in a central portion within the processing vessel 150. The spin chuck 160 includes a horizontal upper surface on which, e.g., suction holes (not shown) for suctioning the wafer $W_U$ (or $W_L$) are formed. Using the suction force of the suction holes, the spin chuck 160 can adsorb the wafer $W_U$ (or $W_L$).

A chuck drive unit 161 equipped with, e.g., an electric motor, is installed below the spin chuck 160. The spin chuck 160 can be rotated at a predetermined speed by the chuck drive unit 161. The chuck drive unit 161 includes an up-down drive source (not shown) such as a cylinder or the like and can move the spin chuck 160 up and down.

A cup 162 is provided around the spin chuck 160 to receive and collect the liquid dropped or scattered from the wafer $W_U$ (or $W_L$). A discharge pipe 163 configured to drain the collected liquid and an exhaust pipe 164 configured to exhaust the cup 322 and discharge an atmosphere therewithin are connected to the bottom surface of the cup 162.

As shown in FIG. 7, a rail 170 extending in the Y-axis direction (the left-right direction in FIG. 7) is formed at the back side of the cup 162 in the X-axis direction (at the lower side in FIG. 7). The rail 170 extends at the outer side of the cup 162 from the back side (the left side in FIG. 7) to the front side (the right side in FIG. 7) of the cup 162 in the Y-axis direction, for example. A nozzle arm 171 and a scrub arm 172 are mounted in the rail 172.

As shown in FIGS. 6 and 7, the nozzle arm 171 supports a pure water nozzle 173 configured to supply pure water to the wafer $W_U$ (or $W_L$). As shown in FIG. 7, the nozzle arm 171 is movable along the rail 170 by a nozzle drive unit 174. With this configuration, the pure water nozzle 173 is movable from a standby section 175 provided at the front of the outer side of the cup 162 in the Y-axis direction up to above the central portion of the wafer $W_U$ (or $W_L$) positioned within the cup 162, and also is movable above the wafer $W_U$ (or $W_L$) in the diameter direction of the wafer $W_U$ (or $W_L$). The nozzle arm 171 is freely moved up and down by operating the nozzle drive unit 174 to adjust the height of the pure water nozzle 173.

As shown in FIG. 6, a supply pipe 176 configured to supply the pure water to the pure water nozzle 173 is connected to the pure water nozzle 173. The supply pipe 176 is in communication with a pure water supply source 177 to store the pure water therein. Further, a supply kit 178 including a valve, a flow rate regulator or the like, which controls a flow of the pure water, is installed in the supply pipe 176.

The scrub arm 172 supports a scrub cleaning tool 180. For example, a plurality of brushes 180a having a string-like or a sponge-like are formed at a leading end of the scrub cleaning tool 180. The scrub arm 172 is movable along the rail 170 by a cleaning tool drive unit 181 as shown in FIG. 7. With this configuration, the scrub cleaning tool 180 is movable from the back of the outer side of the cup 162 in the Y-axis direction up to above the central portion of the wafer $W_U$ (or $W_L$) positioned within the cup 162. Further, the scrub arm 172 is freely moved up and down by the cleaning tool drive unit 181 to adjust the height of the scrub cleaning tool 180.

In the above configuration, the pure water nozzle 173 and the scrub cleaning tool 180 have been described to be supported by their respective arms 171 and 172, but may be supported by a single arm. In one embodiment, the pure water may be supplied from the scrub cleaning tool 180 without the pure water nozzle 173. In some embodiments, a discharge pipe to discharge the liquid and an exhaust pipe to exhaust the internal atmosphere of the processing vessel 150 may be connected to the bottom surface of the processing vessel 150, without the cup 162. In some embodiments, the surface hydrophilization device 40 as configured as above may include an antistatic ionizer (not shown).

Figure 8:
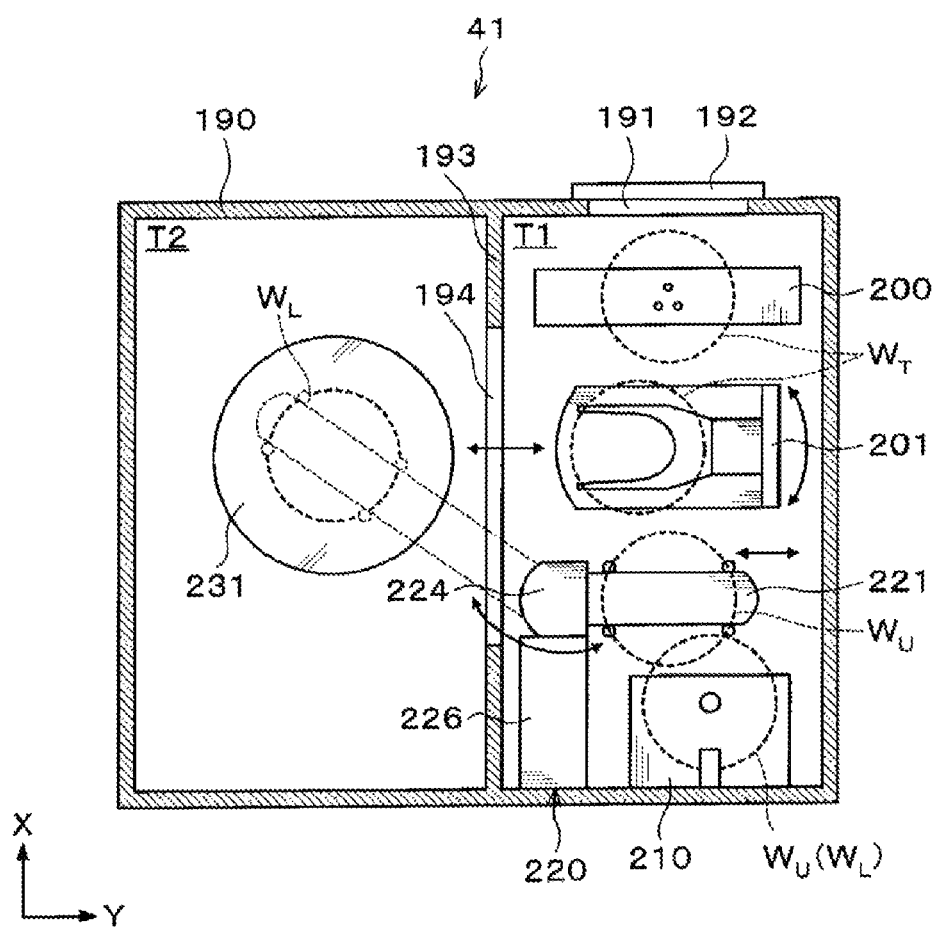
FIG. 8 is a traverse sectional view schematically showing a configuration of a bonding device.

Next, a configuration of the abovementioned bonding device 41 will be described. As shown in FIG. 8, the bonding device 41 includes an internally-sealable processing vessel 190. An inlet/outlet 191, through which the wafer $W_U$ (or $W_L$) and the overlapped wafer $W_T$ are transferred, is formed at a lateral side facing the wafer transfer zone 60 in the processing vessel 190, and an opening/closing shutter 192 is provided in the inlet/outlet 191.

The interior of the processing vessel 190 is partitioned into a transfer region T1 and a processing region T2 by an internal wall 193. The inlet/outlet 191 as described above is formed in the lateral side of the processing vessel 190 in the transfer region T1. Further, an inlet/outlet 194, through which the wafer $W_U$ (or $W_L$) and the overlapped wafer $W_T$ are transferred, is formed in the internal wall 193.

A transition 200, on which the wafer $W_U$ (or $W_L$) and the overlapped wafer $W_T$ are temporarily loaded, is formed in the forward side (the top side in FIG. 8) of the transfer region T1 in the X-axis direction. The transition 200 is formed in, e.g., two stages to simultaneously load any two of the wafers $W_U$ and $W_L$ and the overlapped wafer $W_T$ thereon.

Figure 9:
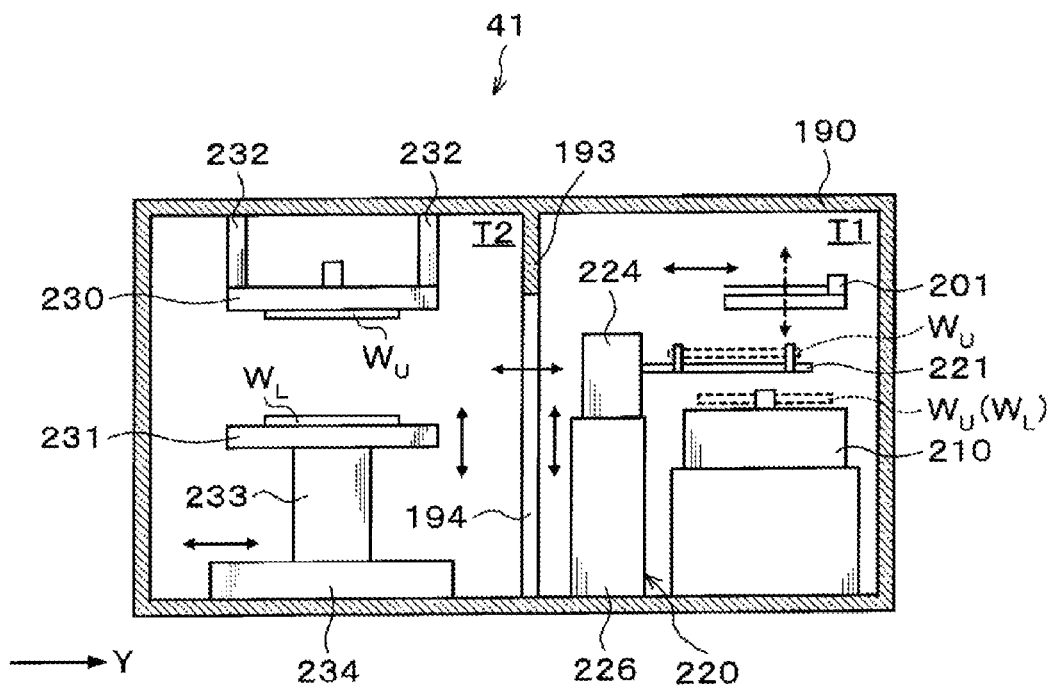
FIG. 9 is a longitudinal sectional view schematically showing the configuration of the bonding device.

A wafer transfer mechanism 201 is provided in the transfer region T1. As shown in FIGS. 8 and 9, the wafer transfer mechanism 201 is equipped with a transfer arm which is movable in vertical and horizontal directions (the Y-axis and X-axis directions) and is rotatable around a vertical axis. The wafer transfer mechanism 201 can transfer the wafer $W_U$ (or $W_L$) and the overlapped wafer $W_T$ within the transfer region T1 or between the transfer region T1 and the processing region T2.

Figure 10:
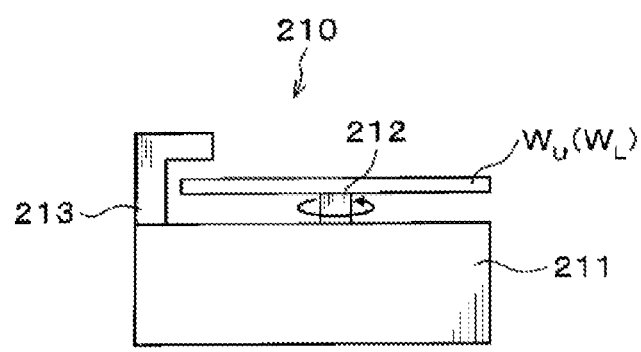
FIG. 10 is a side view schematically showing a configuration of a position adjusting mechanism.

A position adjusting mechanism 210 configured to adjust a horizontal orientation of the wafer $W_U$ (or $W_L$) is disposed at the back side of the transfer region T1 in the X-axis direction (at the bottom side in FIG. 8). As shown in FIG. 10, the position adjusting mechanism 210 is equipped with a base table 211, a holding unit 212 configured to adsorb and rotate the wafer $W_U$ (or $W_L$), and a detection unit 213 configured to detect a position of a notch portion formed in the wafer $W_U$ (or $W_L$). In the position adjusting mechanism 210, the detection unit 213 detects the position of the notch portion of the wafer $W_U$ (or $W_L$), while rotating the wafer $W_U$ (or $W_L$) that is adsorbed to the holding unit 212 such that the position of the notch portion is adjusted. Thus, the position adjusting mechanism 210 adjusts the horizontal orientation of the wafer $W_U$ (or $W_L$).

Figure 11:
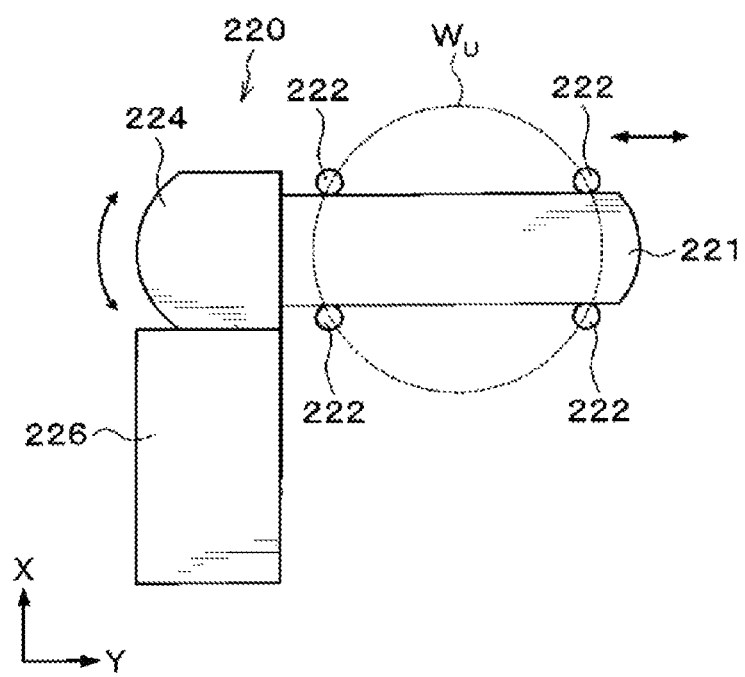
FIG. 11 is a plane view schematically showing a configuration of an inverting mechanism.
Figure 12:
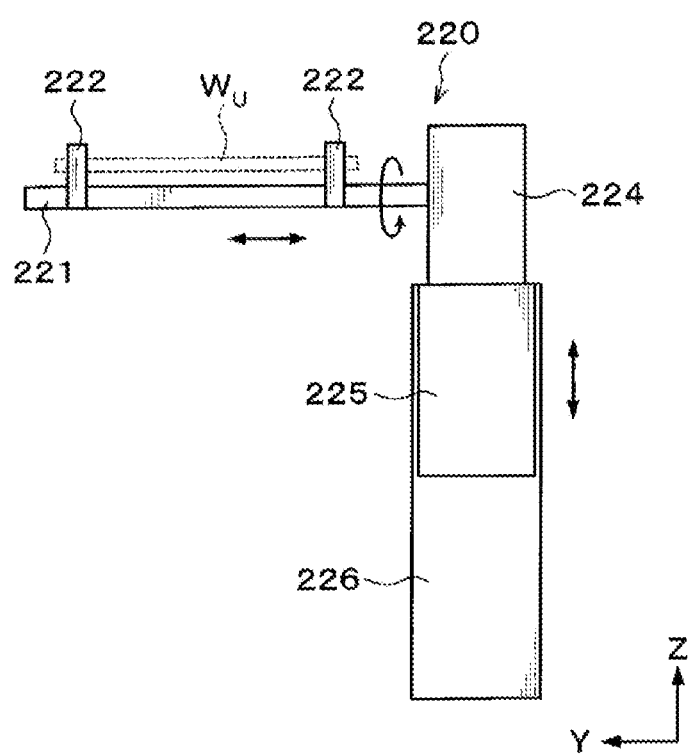
FIG. 12 is a side view schematically showing the configuration of the inverting mechanism.
Figure 13:
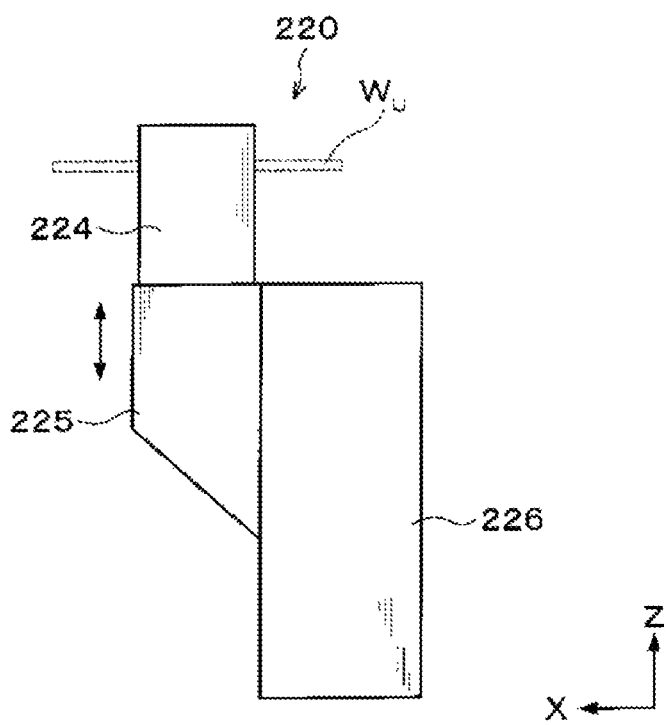
FIG. 13 is another side view schematically showing the configuration of the inverting mechanism.
Figure 14:
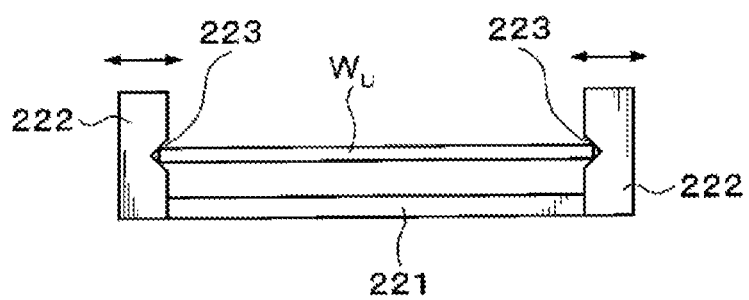
FIG. 14 is a side view schematically showing configurations of a holding arm and a holding member.

In addition, an inverting mechanism 220 configured to invert the front and rear surfaces $W_{U1}$ and $W_{U2}$ of the upper wafer $W_U$ is provided in the transfer region T1. As shown in FIGS. 11 to 13, the inverting mechanism 220 is equipped with a holding arm 221 to hold, e.g., the upper wafer $W_U$. The holding arm 221 is configured to extend in the horizontal direction (the Y-axis direction in FIGS. 11 and 12). Further, the holding arm 221 includes a plurality of (e.g., four) holding members 222 to hold the upper wafer $W_U$. As shown in FIG. 14, the holding members 222 are horizontally movable with respect to the holding arm 221. A cutout 223 configured to hold the periphery of the upper wafer $W_U$ is formed at a lateral side of each of the holding members 222. With this configuration, the holding members 222 can hold the upper wafer $W_U$ while inserting the same into the cutouts 223.

As shown in FIGS. 11 to 13, the holding arm 221 is supported by a first drive unit 224 equipped with, e.g., a motor. The first drive unit 224 allows the holding arm 221 to be rotatable around a horizontal axis. Further, the holding arm 221 is rotatable around the first drive unit 224 and also is movable in the horizontal direction (the Y-axis direction in FIGS. 11 and 12). A second drive unit 225 equipped with, e.g., a motor, is installed below the first drive unit 224. The second drive unit 225 allows the first drive unit 224 to vertically move along a vertically-extended support column 226. With this configuration, the first drive unit 224 and the second drive unit 225 allow the upper wafer $W_U$ held by the holding members 222 to rotate around the horizontal axis and move in the vertical and horizontal directions. In addition, the upper wafer $W_U$ held by the holding members 222 is rotatable around the first drive unit 224 such that it can be moved between the position adjusting mechanism 210 and an upper chuck 230, which will be described later.

As shown in FIGS. 8 and 9, the upper chuck 230 configured to hold the upper wafer $W_U$ on its bottom surface and a lower chuck 231 configured to hold the lower wafer $W_L$ on its upper surface are provided in the processing region T2. The lower chuck 231 is disposed below the upper chuck 230 while being positioned to face the upper chuck 230. That is, the upper wafer $W_U$ held by the upper chuck 230 and the lower wafer $W_L$ held by the lower chuck 231 are disposed opposite from each other.

As shown in FIG. 9, the upper chuck 230 is supported by support members 232 installed in the ceiling of the processing vessel 190. The support members 232 support the periphery of the upper surface of the upper chuck 230. A chuck drive unit 234 is installed below the lower chuck 231 via a shaft 233. The chuck drive unit 234 is configured to move the lower chuck 231 both vertical and horizontal directions. Further, the chuck drive unit 234 is configured to rotate the lower chuck 231 around a vertical axis. In addition, a plurality of elevating pins (not shown) which elevates the lower wafer $W_L$ supported from the bottom are disposed below the lower chuck 231. These elevating pins are inserted into through-holes (not shown) formed in the lower chuck 231 in such a manner that they project from the upper surface of the lower chuck 231.

Figure 15:
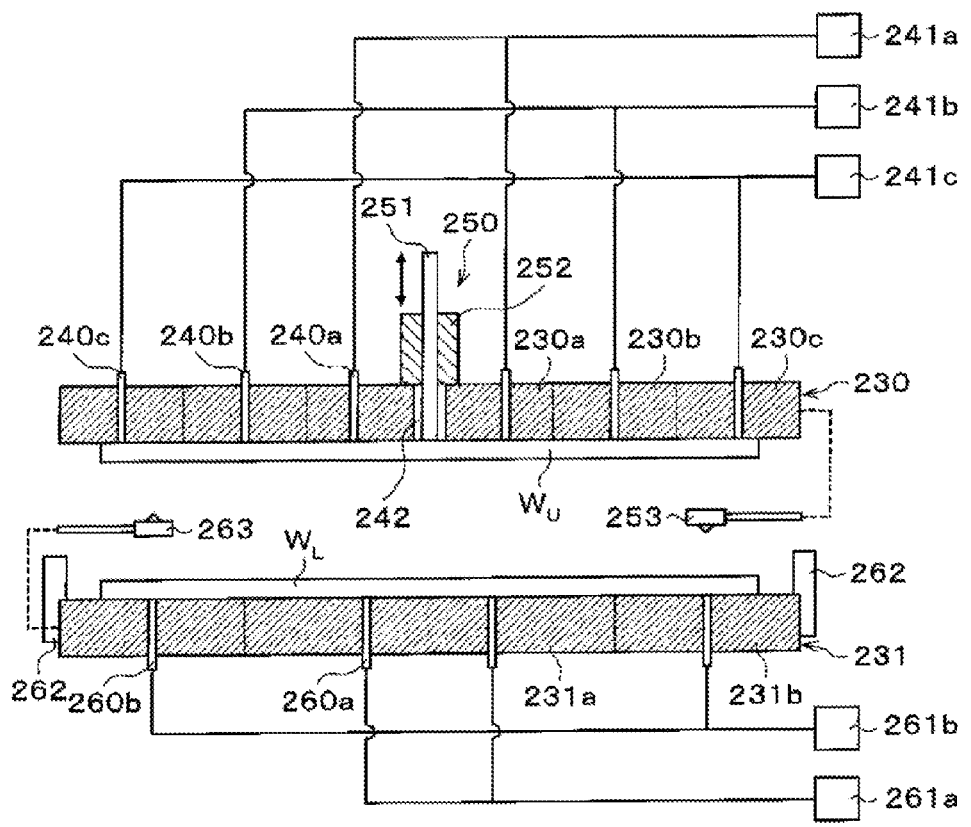
FIG. 15 is a longitudinal sectional view schematically showing configurations of an upper chuck and a lower chuck.
Figure 16:
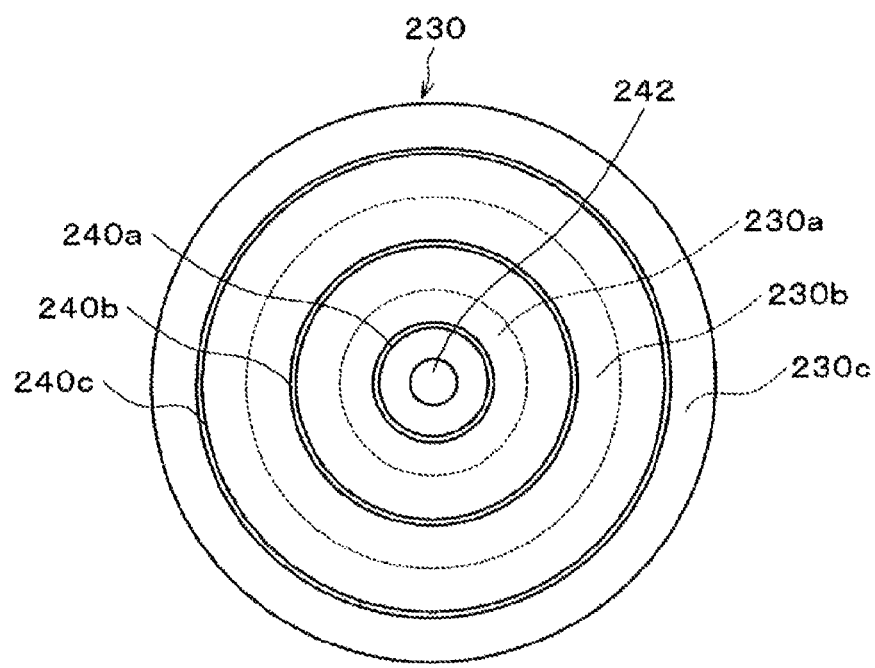
FIG. 16 is a plane view of the upper chuck when viewed from the bottom.

As shown in FIG. 15, the upper chuck 230 is configured to include a plurality of (e.g., three) partitioned regions 230a, 230b and 230c. As shown in FIG. 16, the regions 230a, 230b and 230c are arranged from the center toward the periphery of the upper chuck 230 in that order. The region 230a is of a circular shape and the regions 230b and 230c are of an annular shape, when viewed from the top. As shown in FIG. 15, the regions 230a, 230b and 230c includes respective suction pipes 240a, 240b and 240c which are configured to adsorb the upper wafer $W_U$, respectively. Each of the suction pipes 240a, 240b and 240c are connected to different vacuum pumps 241a, 241b and 241c. Thus, the upper chuck 230 is configured to adsorb the upper wafer $W_U$ by an evacuation force of each of the suction pipes 240a, 240b and 240c installed in the regions 230a, 230b and 230c.

In the following description, each of the regions 230a, 230b and 230c will be sometimes referred to as a first region 230a, a second region 230b and a third region 230c. Further, each of the suction pipes 240a, 240b and 240c will be sometimes referred to as a first suction pipe 240a, a second suction pipe 240b and a third suction pipe 240c. In addition, each of the vacuum pumps 241a, 241b and 241c will be sometimes referred to as a first vacuum pump 241a, a second vacuum pump 241b and a third vacuum pump 241c.

A through-hole 242 passing through the upper chuck 230 in its thickness direction is formed in the central portion of the upper chuck 230. The central portion of the upper chuck 230 corresponds to the central portion of the upper wafer $W_U$ adsorbed to the upper chuck 230. A pressing pin 251 of a pressing member 250 (which will be described later) inserts through the through-hole 242.

The pressing member 250 configured to press the central portion of the upper wafer $W_U$ is disposed on the upper surface of the upper chuck 230. The pressing member 250 is of a cylindrical shape and includes the pressing pin 251 and an outer tube 252 acting as a guide when the pressing pin 251 is elevated. The pressing pin 251 is configured to insert through the through-hole 242 and vertically elevate by a drive unit (not shown) equipped with, e.g., a motor. Further, the pressing member 250 is configured to press the central portion of the upper wafer $W_U$ and the central portion of the lower wafer $W_L$ while being brought into them contact with each other, when the upper wafer $W_U$ and the lower wafer $W_L$ are bonded together, which will be described later.

An upper pickup member 253 configured to pick up an image of the front surface $W_{L1}$ of the lower wafer $W_L$ is disposed in the upper chuck 230. Examples of the upper pickup member 253 may include a wide-angle CCD (Charge-Coupled Device) camera. In some embodiments, the upper pickup member 253 may be disposed above the upper chuck 230.

Figure 17:
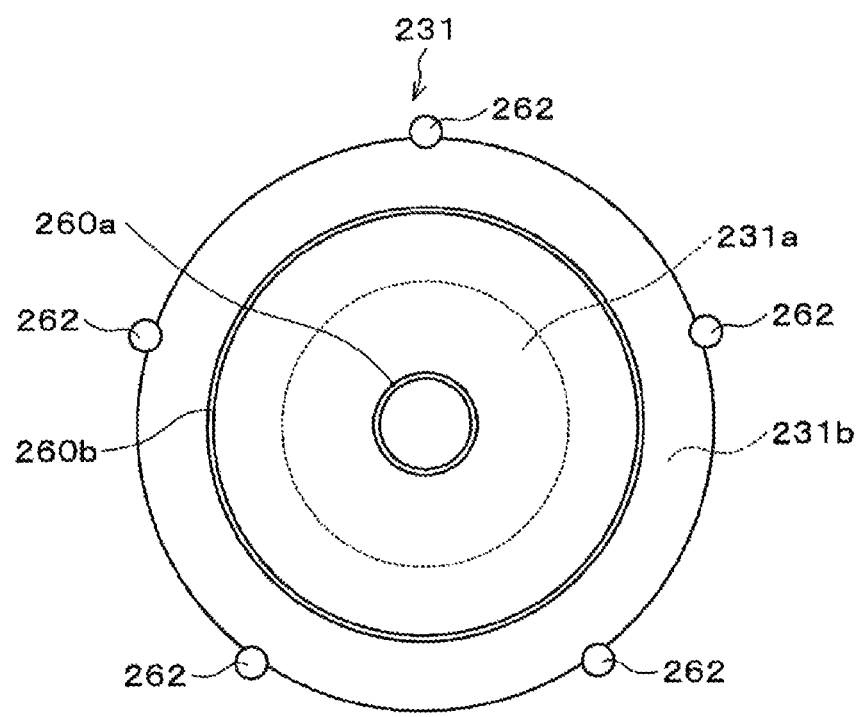
FIG. 17 is a plane view of the lower chuck when viewed from the top.

As shown in FIG. 17, the lower chuck 231 is configured to have a plurality of (e.g., two) partitioned regions 231a and 231b. These regions 231a and 231b are arranged from the center toward the periphery of the lower chuck 231 in that order. The region 231a is of a circular shape and the region 231b is of an annular shape, when viewed from the top. As shown in FIG. 15, the regions 231a and 231b include respective suction pipes 260a and 260b which are configured to adsorb the lower wafer $W_L$, respectively. Each of the suction pipes 260a and 260b are connected to different vacuum pumps 261a and 261b. Thus, the lower chuck 231 adsorbs the lower wafer $W_L$ by an evacuation force of each of the suction pipes 260a and 260b installed in the regions 231a and 231b.

At the periphery of the lower chuck 231 are disposed stopper members 262 configured to prevent the wafers $W_U$, $W_L$ or $W_T$ from being jumped out or slipped from the lower chuck 231. The stopper members 262 are formed to vertically extend upward in such a manner that their top sides are positioned at a higher position than a height of the overlapped wafer $W_T$ loaded on the lower chuck 231. In this embodiment, as shown in FIG. 17, the stopper members 262 are disposed at five places in the periphery of the lower chuck 231.

A lower pickup member 263 configured to pick up an image of the front surface $W_{U1}$ of the upper wafer $W_U$ is disposed in the lower chuck 231. Examples of the lower pickup member 263 may include a wide-angle CCD camera. In some embodiments, the lower pickup member 263 may be disposed above the lower chuck 231.

Figure 18:
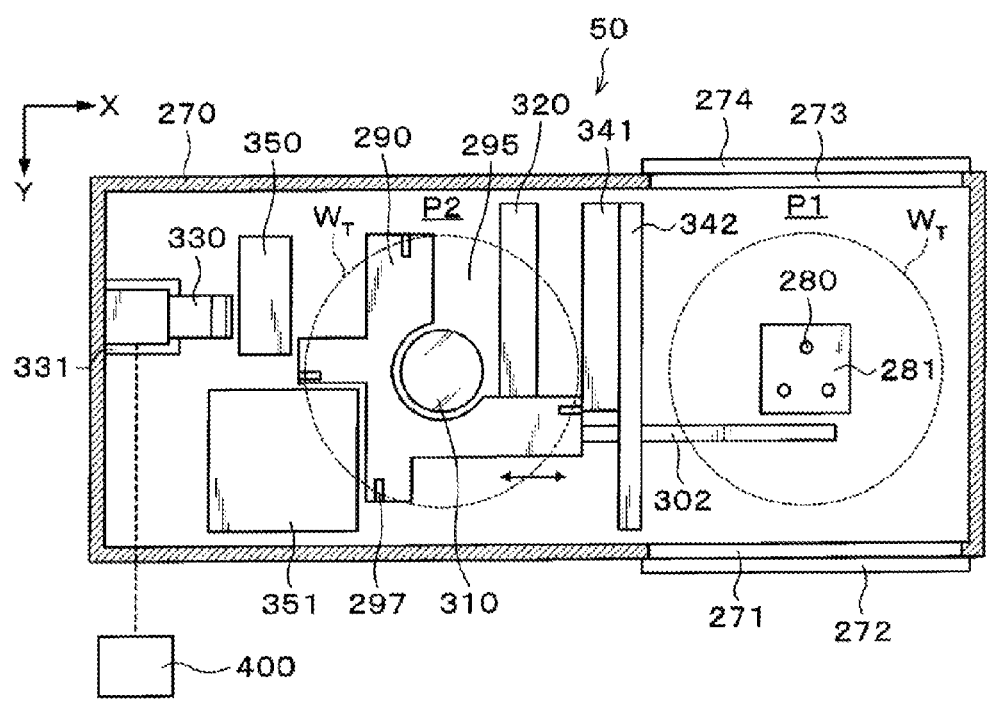
FIG. 18 is a traverse sectional view schematically showing a configuration of an inspection device.
Figure 19:
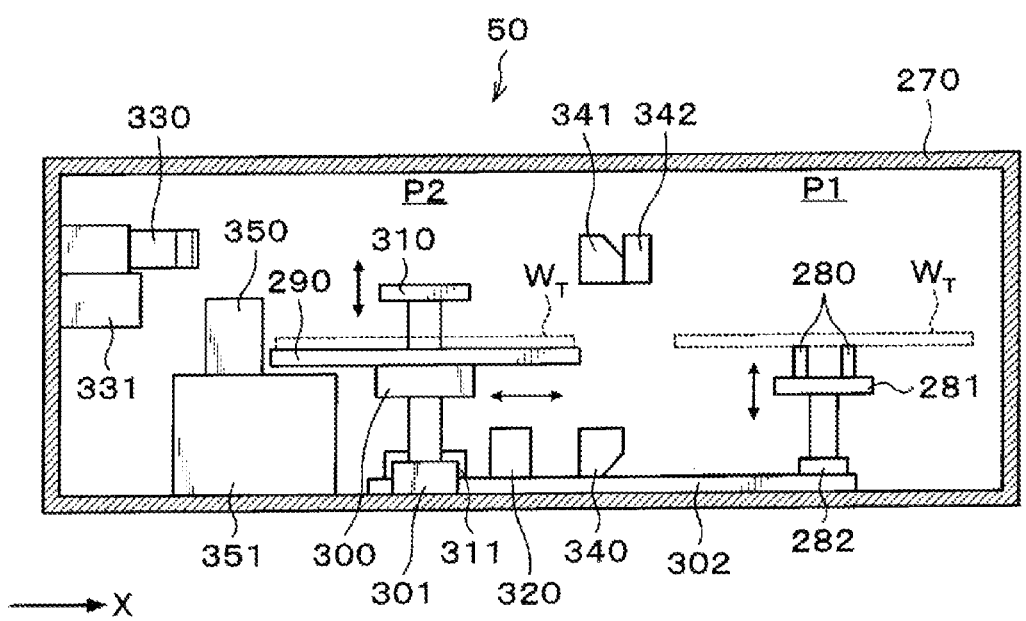
FIG. 19 is a longitudinal sectional view schematically showing the configuration of the inspection device.

Next, a configuration of the aforementioned inspection device 50 will be described. As shown in FIGS. 18 and 19, the inspection device 50 includes a processing vessel 270. An inlet/outlet 271, through which the overlapped wafer $W_T$ is transferred, is formed in a lateral side facing the wafer transfer zone 60 in the processing vessel 270, and an opening/closing shutter 272 is installed at the inlet/outlet 271. In addition, an inlet/outlet 273, through which the overlapped wafer $W_T$ is transferred, is formed in a lateral side facing the carry-in/carry-out station 2 in the processing vessel 270, and an opening/closing shutter 274 is installed at the inlet/outlet 273.

Between the inlet/outlets 271 and 273 within the processing vessel 270 (at the right side in FIGS. 18 and 19) are disposed elevating pins 280 which are configured to transfer the overlapped wafer $W_T$ to the wafer transfer unit 61 disposed outside, and also transfer the overlapped wafer $W_T$ to a first holding unit 290 (which will be described later). In this embodiment, three elevating pins 280 are provided on a holding member 281. The elevating pins 280 can be elevated by an elevation drive unit 282 equipped with, e.g., a motor.

Figure 20:
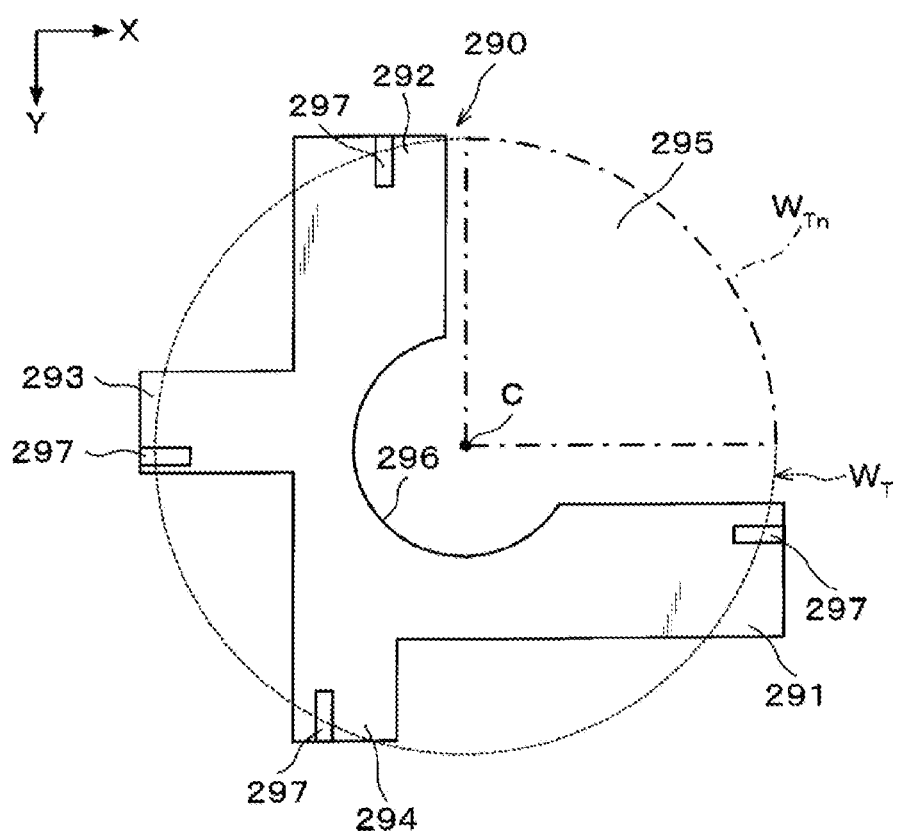
FIG. 20 is a plane view schematically showing a configuration of a first holding unit.

The first holding unit 290 as another holding unit, which is configured to hold a rear surface of the overlapped wafer $W_T$, is provided within the processing vessel 270. As shown in FIG. 20, the first holding unit 290 includes four support members 291 to 294 having a substantially rectangular shape when viewed from the top. These support members 291 to 294 are arranged to extend in a direction orthogonal to each other when viewed from the top. Specifically, as shown in FIG. 20, the support members 291 and 293 are arranged in the X-axis direction and the support members 292 and 294 are arranged in the Y-axis direction. In the following description, the support members 291 to 294 will be sometimes referred to as a first support member 291, a second support member 292, a third support member 293 and a fourth support member 294, respectively.

In the first holding unit 290, the overlapped wafer $W_T$ is held such that its center C is positioned between the first support member 291 and the second member 292. In addition, a cutout 295 to expose a ¼ portion of the rear surface of the overlapped wafer $W_T$ therethrough is formed between the first support member 291 and the second support member 292. In FIG. 20, the exposed portion of the rear surface of the overlapped wafer $W_T$ is indicated by an alternate long and short dash line. In the following description, the exposed portion of the overlapped wafer $W_T$ through the cutout 295 will be sometimes referred to as an overlapped wafer $W_{Tn}$ (n is an integer of 1 to 4). Further, a curved portion 296 curved along a periphery of a second holding unit 310 (which will be described later) is formed in sides of the first support member 291 and the second support member 292.

In addition, holding members 297 configured to hold the rear surface of the overlapped wafer $W_T$ are formed on leading ends of the support members 291 to 294, respectively. These holding members 297 are arranged such that an angle between adjacent holding members 297 and the center of the overlapped wafer $W_T$ is smaller than 120 degrees. This allows the overlapped wafer $W_T$ to be stably held by the first holding unit 290. In some embodiments, examples of the holding members 297 may include a resin O-ring or a support pin. For the resin O-ring, the holding members 297 hold the rear surface of the overlapped wafer $W_T$ by a friction between the holding members 297 and the rear surface of the overlapped wafer $W_T$.

As shown in FIG. 19, the first holding unit 290 is connected to a drive unit 301 via a member 300. The drive unit 301 is equipped with, e.g., a motor (not shown). A rail 302 extending in the X-axis direction in FIGS. 18 and 19 is disposed on the bottom of the processing vessel 270. The drive unit 301 is mounted on the rail 302. Along the rail 302, the first holding unit 290 (or the drive unit 301) is movable between a transfer sector P1 at which the overlapped wafer $W_T$ is transferred to the elevating pins 280, and an inspection sector P2 at which a bonding state of the overlapped wafer $W_T$ is inspected by a displacement gauge 350, which will be described later.

The second holding unit 310 configured to hold and rotate the overlapped wafer $W_T$ is provided within the processing vessel 270. The second holding unit 310 is disposed at the inspection sector P2. The second holding unit 310 has a horizontal upper surface on which suction holes (not shown) for suctioning the overlapped wafer $W_T$. Using the suction force of the suction holes, the second holding unit 310 can adsorb the overlapped wafer $W_T$.

The second holding unit 310 is connected to a drive unit 311 equipped with, e.g., a motor. The second holding unit 310 is rotatable with the operation of the drive unit 311. The drive unit 311 is equipped with an elevation drive source such as a cylinder or the like and can move the second holding unit 310 up and down. When the first holding unit 290 is at the inspection sector P2, the second holding unit 310 does not interfere with the first holding unit 290 by virtue of the curved portion 296 formed in the first holding unit 290 even when the second holding unit 310 is moved up and down.

Within the processing vessel 270 is provided an infrared irradiating unit 320 configured to irradiate an infrared ray onto the exposed portion of the rear surface of the overlapped wafer $W_T$ (i.e., the overlapped wafer $W_{Tn}$), which is exposed through the cutout 295 of the first holding unit 290. The infrared irradiating unit 320 is disposed between the transfer sector P1 and the inspection sector P2 and below the first holding unit 290 and the second holding unit 310. Further, the infrared irradiating unit 320 is configured to extend in the Y-axis direction to be longer than at least a radial width of the overlapped wafer $W_{Tn}$. A wavelength of the infrared ray irradiated from the infrared irradiating unit 320 falls within a range of 1,100 nm to 2,000 nm. The infrared ray of such a wavelength transmits through the overlapped wafer $W_{Tn}$.

Further, within the processing vessel 270 is provided an image pickup unit 330 configured to receive the infrared ray irradiated from the infrared irradiating unit 320 and pick up images of the exposed portions of the rear surface of the overlapped wafer $W_T$ held by the first holding unit 290, which are exposed through the cutout 295. Specifically, the image pickup unit 330 picks up the images of the overlapped wafer $W_{Tn}$. Examples of the image pickup unit 330 may include an infrared camera. The image pickup unit 330 is disposed at the backside of the processing vessel 270 in the X-axis direction (i.e., at the left side in FIGS. 18 and 19) and above the first holding unit 290 and the second holding unit 310. Further, the image pickup unit 330 is supported by a support member 331. The image pickup unit 330 is connected to the controller 400 (which will be described later). The picked-up images of the overlapped wafer $W_{Tn}$ by the image pickup unit 330 are sent to the controller 400 in which the picked-up images are combined to create a single whole image of the overlapped wafer $W_T$.

First and second direction changing units 340 and 341, which are configured to change a traveling direction of the infrared ray between the infrared irradiating unit 320 and the image pickup unit 330, are disposed inside the processing vessel 270. The first and second direction changing units 340 and 341 are disposed opposite to each other at a position (at the forward side of the X-axis direction in FIGS. 18 and 19) facing the infrared irradiating unit 320 inside the transfer sector P1. The first direction changing unit 340 is disposed below the first holding unit 290 and the second holding unit 310, while the second direction changing unit 341 is disposed above the first holding unit 290 and the second holding unit 310. Further, the first and second direction changing units 340 and 341 are arranged to extend in the Y-axis direction, like the infrared irradiating unit 320. The second direction changing unit 341 is supported by a support member 342 extending in the Y-axis direction.

Figure 21:
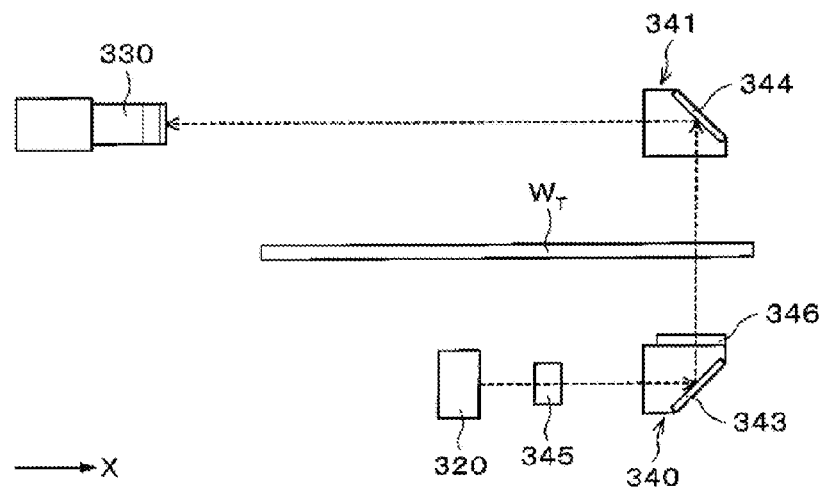
FIG. 21 is a view showing a path of an infrared ray traveling between an infrared irradiation unit and an image pickup unit.
Figure 22:
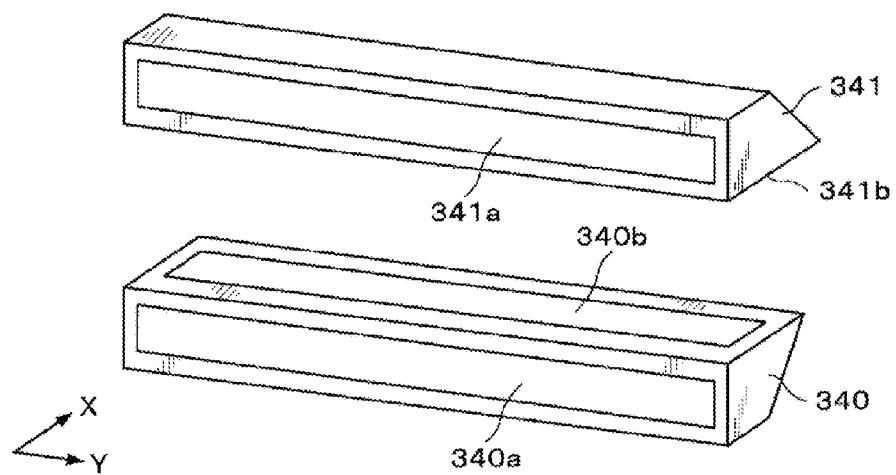
FIG. 22 is a perspective view schematically showing configurations of a first direction changing unit and a second direction changing unit.

As shown in FIG. 21, a first reflection mirror 343 is installed in the first direction changing unit 340. The first reflection mirror 343 is arranged to be inclined by 45 degrees with respect to a horizontal axis. The infrared ray irradiated from the infrared irradiating unit 320 is reflected at the first reflection mirror 343 and then vertically travels upward. As shown in FIG. 22, openings 340a and 340b through which the infrared ray passes are formed in lateral and upper sides of the first direction changing unit 340, respectively.

Similarly, as shown in FIG. 21, a second reflection mirror 344 is installed in the second direction changing unit 341. The second reflection mirror 344 is arranged to be inclined by 45 degrees with respect to a horizontal axis. The infrared ray reflected at the first direction changing unit 340 is further reflected at the second reflection mirror 344 and then horizontally travels. As shown in FIG. 22, openings 341a and 341b through which the reflected infrared ray passes are formed in lateral and lower sides of the second direction changing unit 341, respectively.

As shown in FIG. 21, a cylindrical lens 345 configured to collect the infrared ray to be irradiated onto the overlapped wafer $W_T$ is disposed between the infrared irradiating unit 320 and the first direction changing unit 340. Further, a diffusion plate 346, which is configured to establish a uniformity in-plane diffusion of the infrared ray collected by the cylindrical lens 345 onto the overlapped wafer $W_T$, is mounted on the upper side of the first direction changing unit 340.

With this configuration, the infrared ray irradiated from the infrared irradiating unit 320 transmits the overlapped wafer $W_T$ through a series of the cylindrical lens 345, the first reflection mirror 343 and the diffusion plate 346 and subsequently, is directed to the image pickup unit 330 through the second reflection mirror 344 of the second direction changing unit 341.

As shown in FIGS. 18 and 19, the displacement gauge 350, which is configured to measure a displacement of a peripheral side of the overlapped wafer $W_T$ held by the second holding unit 310, is installed inside the processing vessel 270. The displacement gauge 350 is disposed at the backside of the inspection sector P2 in the X-axis direction. The displacement gauge 350 is not limited thereto as long as it can measure the displacement of the peripheral side of the overlapped wafer $W_T$. In this embodiment, a laser displacement gauge is used as the displacement gauge 350.

Figure 23:
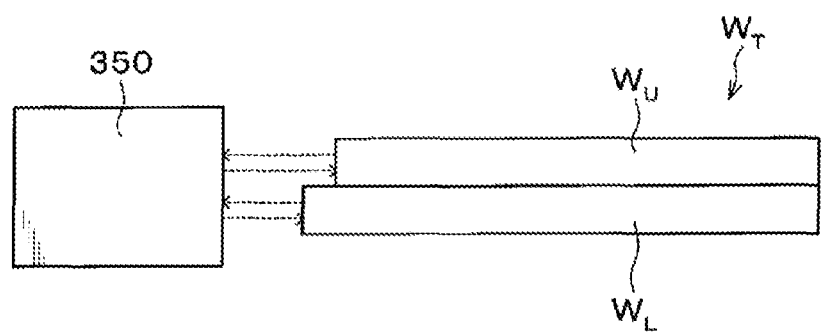
FIG. 23 is an explanatory view showing how to measure displacements of peripheral sides of an upper wafer and a lower wafer using a displacement gauge.

As shown in FIG. 23, the displacement gauge 350 irradiates laser beams onto peripheral sides of the upper wafer $W_U$ and the lower wafer $W_L$ making up the overlapped wafer $W_T$, and receives the laser beams reflected therefrom, thereby measuring displacements of the peripheral sides of the upper wafer $W_U$ and the lower wafer $W_L$. While rotating the overlapped wafer $W_T$ with the second holding unit 310, the displacement gauge 350 irradiates the laser beams onto the peripheral sides of the upper wafer $W_U$ and the lower wafer $W_L$. By doing so, the displacements of the entire peripheral sides of the upper wafer $W_U$ and the lower wafer $W_L$ are measured such that a misalignment between the upper wafer $W_U$ and the lower wafer $W_L$ is inspected.

Figure 24:
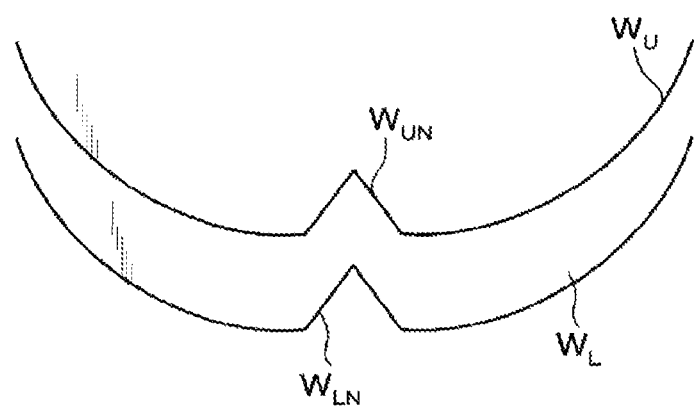
FIG. 24 is an explanatory view showing how to measure a misalignment between notch portions of the upper wafer and the lower wafer.

As shown in FIG. 24, the displacement gauge 350 further measures a misalignment between a notch portion $W_{UN}$ of the upper wafer $W_U$ and a notch portion $W_{LN}$ of the lower wafer $W_L$. Specifically, the displacement gauge 350 measures the misalignment between vertexes of the notch portions $W_{UN}$ and $W_{LN}$. This makes it possible to inspect horizontal and vertical misalignments between the upper wafer $W_U$ and the lower wafer $W_L$.

As shown in FIGS. 18 and 19, a position detecting mechanism 351 configured to detect a position of the overlapped wafer $W_T$ held by the second holding unit 310 is installed inside the processing vessel 270. The position detecting mechanism 351 is arranged adjacent to the third support member 293 and the fourth support member 294 of the first holding unit 290. The position detecting mechanism 351, which is equipped with, e.g., a CCD camera (not shown), detects positions of the notch portions of the overlapped wafer $W_T$ held by the second holding unit 310. While rotating the second holding unit 310, the position detecting mechanism 351 detects and adjusts the positions of the notch portions of the overlapped wafer $W_T$.

The bonding system 1 includes the controller 400 as shown in FIG. 1. The control unit 200 is, for example, a computer and includes a program storage (not shown). The program storage stores a program which controls processing of the wafers $W_U$ and $W_L$, and the overlapped wafer $W_T$ in the bonding system 1. The program storage also stores a program which controls operation of a driving system including the above-described processing units and transfer units to implement a bonding process in a bonding system 1, which will be described below. The programs may be installed in the controller 400 from a computer readable storage medium H such as, for example, a hard disk (HD), a flexible disk (FD), a compact disk (CD), a magneto-optical disk (MO), a memory card or the like.

Figure 25:
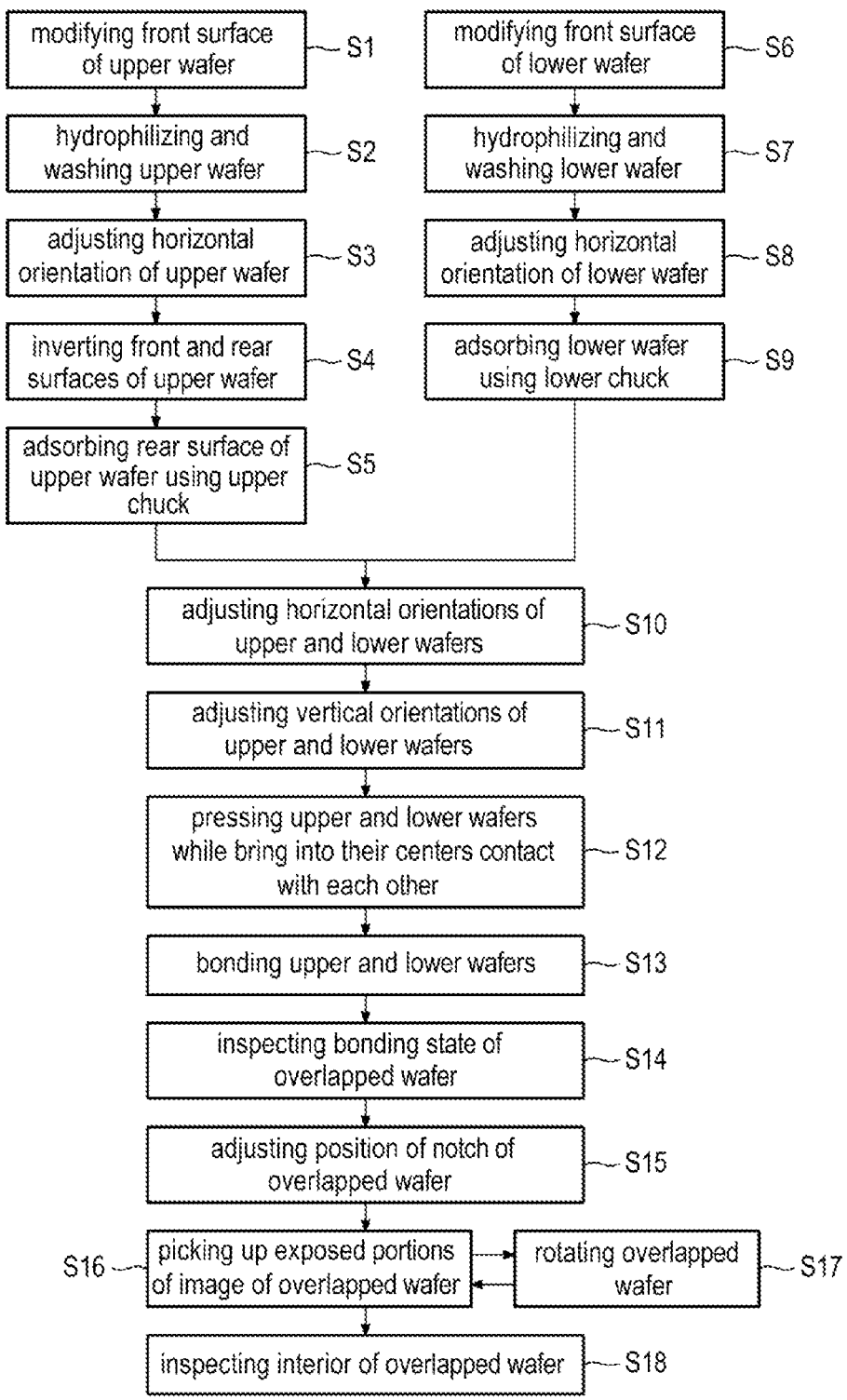
FIG. 25 is a flowchart showing main operations of a wafer bonding process.

Next, a bonding process of the wafers $W_U$ and $W_L$ and an inspection process of the overlapped wafer $W_T$ using the bonding system 1 configured as above will be described. FIG. 25 is a flow chart showing main operations of the bonding process.

First, the cassette $C_U$ with a plurality of upper wafers $W_U$, a cassette $C_s$ with a plurality of lower wafers $W_L$, and an empty cassette $C_T$ are loaded on a respective cassette loading board 11 of the carry-in/carry-out station 2. Thereafter, the upper wafer $W_U$ within the cassette $C_U$ is taken out by the wafer transfer unit 22, and then is transferred to the transition unit 51 of the third processing block G3 of the processing station 3.

Subsequently, the upper wafer $W_U$ is transferred to the surface modification device 30 of the first processing block G1 by the wafer transfer unit 61. The upper wafer $W_U$ transferred to the surface modification device 30 is loaded on the loading table 110 by the wafer transfer unit 61. Thereafter, the wafer transfer unit 61 is retreated from the surface modification device 30 and the gate valve 102 is closed. The upper wafer $W_U$ loaded on the loading table 110 is maintained at a predetermined temperature, for example, in the range of 25 to 30 degrees C. by the temperature adjusting mechanism 112.

Thereafter, the suction unit 104 is operated to reduce an internal atmosphere of the processing vessel 100 to a predetermined degree of vacuum, for example, 67 to 333 Pa (0.5 to 2.5 Torr) through the air suction hole 103. Then, the internal atmosphere of the processing vessel 100 is kept at the predetermined degree of vacuum during the process of the upper wafer $W_U$, as will be described later.

Thereafter, the oxygen gas is supplied from the gas supply pipe 130 into the plasma generation region R1 within the processing vessel 100. Further, a microwave of, for example, 2.45 GHz, is emitted from the radial line slot antenna 120 into the plasma generation region R1. The emission of the microwave allows the oxygen gas to be excited and plasmalized in the plasma generation region R1, which results in, for example, ionization of the oxygen gas. At this time, some microwaves traveling downward are reflected at the ion conduction structure 140 so that it stays within the plasma generation region R1, which generates high-density plasma therein.

Subsequently, in the ion conduction structure 140, the power supply 145 applies a predetermined voltage across the pair of electrodes 141 and 142. Thus, only the oxygen ions generated in the plasma generation region R1 are transferred through the openings 144 of the ion conduction structure 140 and are introduced into the processing region R2.

At this time, the controller 400 adjusts the voltage applied across the pair of electrodes 141 and 142 to control energy to be applied to the oxygen ions which are transferred through the openings 144. The energy to be applied to the oxygen ions is one sufficient to cut a double bond of $SiO_2$ in the front surface $W_{U1}$ of the upper wafer $W_U$ to generate a single bond of SiO, and is set to a value of a range in which the front surface $W_{U1}$ is not damaged.

At this time, the ampere meter 146 measures a value of current flowing between the pair of electrodes 141 and 142. Based on the measured current value, an amount of the oxygen ions being transferred through the ion conduction structure 140 is detected. Based on the detected amount of oxygen ion passage, the controller 400 controls various parameters such as an amount of supply of the oxygen gas from the gas supply pipe 130, a voltage to be applied across the pair of electrodes 141 and 142, and the like such that the amount of oxygen ion passage reaches a predetermined value.

Thereafter, the oxygen ions introduced into the processing region R2 are irradiated and injected onto the front surface $W_{U1}$ of the upper wafer $W_U$ loaded on the loading table 110. The irradiated oxygen ions cut a double bond of $SiO_2$ in the front surface $W_{U1}$ to generate a single bond of SiO. Further, since the oxygen ions are used in modifying the front surface $W_{U1}$, the oxygen ions irradiated onto the front surface $W_{U1}$ of the upper wafer $W_U$ contribute to the bond of SiO. In this way, the front surface $W_{U1}$ of the upper wafer $W_U$ is modified (Operation S1 in FIG. 25).

Subsequently, the upper wafer $W_U$ is transferred to the surface hydrophilization device 40 of the second processing block G2 by the wafer transfer unit 61. The upper wafer $W_U$ transferred to the surface hydrophilization device 40 is delivered to the spin chuck 160 by the wafer transfer unit 61 and be adsorbed to the spin chuck 160.

Subsequently, the pure water nozzle 173 positioned within the standby section 175 is moved to the central portion of the upper wafer $W_U$ by the nozzle arm 171, and the scrub cleaning tool 180 is moved above the upper wafer $W_U$ by the scrub arm 172. Thereafter, pure water is supplied from the pure water nozzle 173 onto the upper wafer $W_U$ while rotating the upper wafer $W_U$ by the spin chuck 160. Thus, a hydroxyl group (silanol group) is adhered onto the front surface $W_{U1}$ of the upper wafer $W_U$ which is modified by the surface modification device 30 so that the front surface $W_{U1}$ is hydrophilized. Further, the front surface $W_{U1}$ of the upper wafer $W_U$ is cleaned by the scrub cleaning tool 180 and the pure water supplied from the pure water nozzle 173 (Operation S2 in FIG. 25). Some of the pure water supplied onto the front surface $W_{U1}$ of the upper wafer $W_U$ is used to hydrophilize the front surface $W_{U1}$ as described above, that is, to bond the wafers $W_U$ and $W_L$ as will be described later, while other pure water remains on the front surface $W_{U1}$ of the upper wafer $W_U$.

Subsequently, the upper wafer $W_U$ is transferred to the bonding device 41 of the second processing block G2 by the wafer transfer unit 61. In the bonding device 41, the upper wafer $W_U$ is transferred to the position adjusting mechanism 210 by the wafer transfer mechanism 201 via the transition 200. In the position adjusting mechanism 210, a horizontal orientation of the upper wafer $W_U$ is adjusted (Operation S3 in FIG. 25).

Thereafter, the upper wafer $W_U$ is moved from the position adjusting mechanism 210 to the holding arm 221 of the inverting mechanism 220. Subsequently, in the transfer region T1, the holding arm 221 is inverted such that the front and rear surfaces of the upper wafer $W_U$ are inverted upside down (Operation S4 in FIG. 23). That is, the front surface $W_{U1}$ of the upper wafer $W_U$ is oriented downward.

Subsequently, the holding arm 221 of the inverting mechanism 220 rotates around the first driving unit 224 and moves below the upper chuck 230. And then, the upper wafer $W_U$ is transferred from the inverting mechanism 220 to the upper chuck 230. The rear surface $W_{U2}$ of the upper wafer $W_U$ is adsorbed to the upper chuck 230 (Operation S5 in FIG. 25). At this time, all the vacuum pumps 241a, 241b and 241c are operated to suction the upper wafer $W_U$ over all of the regions 230a, 230b and 230c of the upper chuck 230. The upper wafer $W_U$ is on standby in the upper chuck 230 until the lower wafer $W_L$ is transferred to the bonding device 41, which will be described later.

While the operations S1 to S5 as described above are being performed on the upper wafer $W_U$, the lower wafer $W_L$ following that upper wafer $W_U$ is processed. First, the lower wafer $W_L$ is taken out of the cassette $C_L$ by the wafer transfer unit 22 and subsequently, is transferred to the transition unit 51 of the processing station 3.

Subsequently, by the wafer transfer unit 61, the lower wafer $W_L$ is transferred to the surface modification device 30 where the front surface $W_U$ of the lower wafer $W_L$ is modified (Operation S6 in FIG. 25). The modification for the front surface $W_{L1}$ of the lower wafer $W_L$ to be performed in Operation S6 is the same as that in Operation S1, and therefore, a description thereof will be omitted to avoid repetition.

Thereafter, by the wafer transfer unit 61, the lower wafer $W_L$ is transferred to the surface hydrophilization device 40 where the front surface $W_{L1}$ of the lower wafer $W_L$ is hydrophilized and cleaned (Operation S7 in FIG. 25). The hydrophilization and cleaning operation for the front surface $W_{L1}$ of the lower wafer $W_L$ to be performed in Operation S7 is the same as that in Operation S2, and therefore, a description thereof will be omitted to avoid repetition. Some of the pure water supplied onto the front surface $W_{L1}$ of the lower wafer $W_L$ is used to hydrophilize the front surface $W_{L1}$, that is, to bond the wafers $W_U$ and $W_L$ as will be described later, while other pure water remains on the front surface $W_{L1}$ of the lower wafer $W_L$.

Thereafter, the lower wafer $W_L$ is transferred to the bonding device 41 by the wafer transfer unit 61. In the bonding device 41, the lower wafer $W_L$ is transferred to the position adjusting mechanism 210 by the wafer transfer mechanism 201 via the transition 200. In the position adjusting mechanism 210, a horizontal orientation of the lower wafer $W_L$ is adjusted (Operation S8 in FIG. 25).

Thereafter, by the wafer transfer mechanism 201, the lower wafer $W_L$ is transferred to the lower chuck 231 where lower wafer $W_L$ is adsorbed thereto (Operation S9 in FIG. 25). At this time, all the vacuum pumps 261a and 261b are operated to suction the lower wafer $W_L$ over the regions 231a and 231b of the lower chuck 231. Thus, the rear surface $W_{L2}$ of the lower wafer $W_L$ is adsorbed to the lower chuck 231 and the front surface $W_{L1}$ of the lower wafer $W_L$ is oriented upward.

Figure 26:
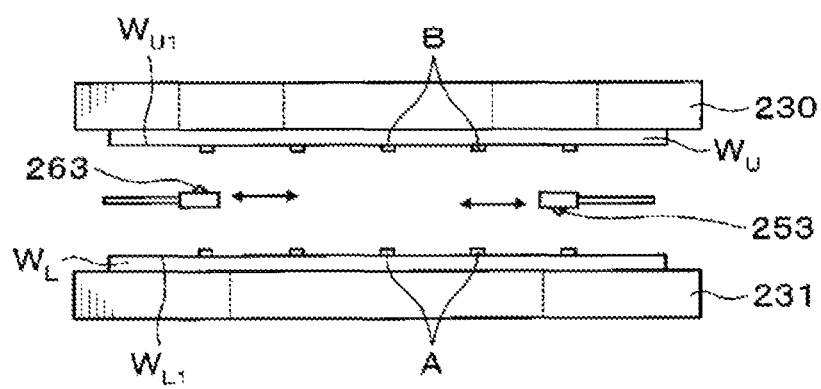
FIG. 26 is an explanatory view showing how to adjust horizontal positions of the upper wafer and the lower wafer.

Subsequently, the horizontal directions of the upper wafer $W_U$ held by the upper chuck 230 and the lower wafer $W_L$ held by the lower chuck 231 are adjusted. As shown in FIG. 26, a plurality of (e.g., four or more) predetermined reference points A are formed on the front surface $W_{L1}$ of the lower wafer $W_L$, and a plurality of (e.g., four or more) predetermined reference points B are formed on the front surface $W_{U1}$ of the lower wafer $W_U$. Predetermined patterns formed on the wafers $W_U$ and $W_L$ may be used as the reference points A and B, respectively. Subsequently, the upper pickup member 253 is horizontally moved to pick up the front surface $W_{L1}$ of the lower wafer $W_L$. Similarly, the lower pickup member 263 is horizontally moved to pick up the front surface $W_{U1}$ of the upper wafer $W_U$. Thereafter, the horizontal position (including the horizontal orientation) of the lower wafer $W_L$ is adjusted by the lower chuck 231 such that positions of the reference points A of the lower wafer $W_L$ indicated on an image picked up by the upper pickup member 253 coincide with positions of the reference points B of the upper wafer $W_U$ indicated on an image picked up by the lower pickup member 263. Specifically, the lower chuck 231 is horizontally moved by the chuck drive unit 234 to adjust the horizontal position of the lower wafer $W_L$. Thus, the horizontal positions of the upper wafer $W_U$ and the lower wafer $W_L$ are adjusted (Operation S10 in FIG. 25). In some embodiments, the lower chuck 231 may be moved without moving the upper pickup member 253 and the lower pickup member 263.

In addition, although the horizontal orientations of the wafers $W_U$ and $W_L$ are adjusted by the position adjusting mechanism 210 in Operations S3 and S8, the horizontal orientations may be finely adjusted even in Operation S10. While in Operation S10 of this embodiment, the predetermined patterns formed on the wafers $W_U$ and $W_L$ are used as the reference points A and B, other reference points may be used. As an example, peripheral portions and the notch portions of the wafers $W_U$ and $W_L$ may be used as the reference points.

Figure 27:
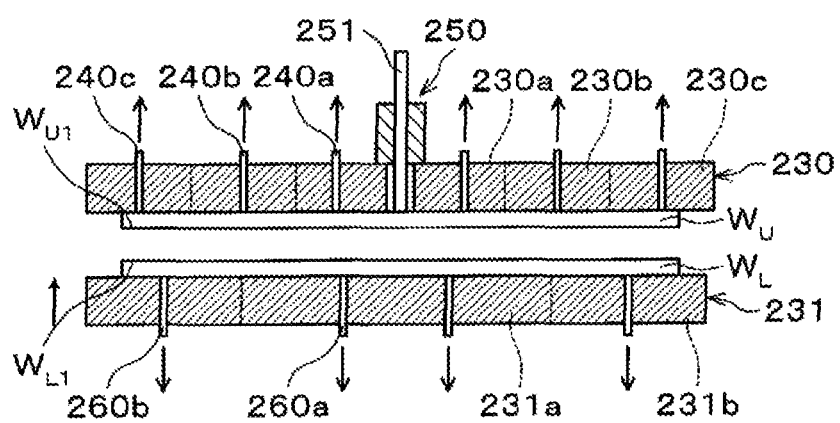
FIG. 27 is an explanatory view showing how to adjust vertical positions of the upper wafer and the lower wafer.

Thereafter, as shown in FIG. 27, the lower chuck 231 is moved upward by the chuck drive unit 234 to place the lower wafer $W_L$ at a predetermined position. In this embodiment, the lower wafer WL is placed such that a gap between the front surface $W_{L1}$ of the lower wafer $W_L$ and the front surface $W_{U1}$ of the lower wafer $W_U$ corresponds to a predetermined distance, e.g., in a range of 80 μm to 200 μm. In this way, the vertical positions of the upper wafer $W_U$ and the lower wafer $W_L$ are adjusted (Operation S11 in FIG. 25). In Operations S5, S10 and S11, the upper wafer $W_U$ is suctioned over the entire regions 230a, 230b and 230c of the upper chuck 230. Similarly, in Operations S9 to S11, the lower wafer $W_L$ is suctioned over the entire regions 231a and 231b of the lower chuck 231.

Figure 28:
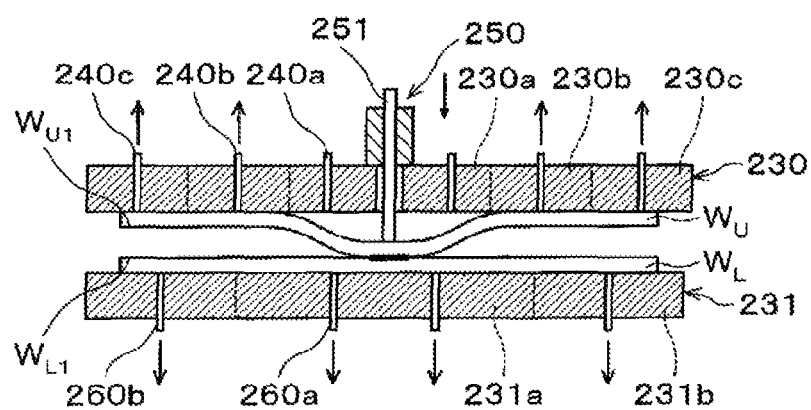
FIG. 28 is an explanatory view showing how to bring central portions of the upper wafer and the lower wafer into contact with each other and to press them.

Thereafter, the first vacuum pump 241a is deactivated to stop the suction of the upper wafer $W_U$ by the first suction pipe 240a in the first region 230a, as shown in FIG. 28. At this time, the upper wafer $W_U$ is suctioned and adsorbed in only the second region 230b and the third region 230c. Subsequently, the pressing pin 251 of the pressing member 250 is moved downward to descend the upper wafer $W_U$ while pressing the central portion of the upper wafer $W_U$. At this time, a load of, e.g., 200 g, is applied to the pressing pin 251, wherein the load causes the pressing pin 251 to be moved by a distance of 70 μm in the absence of upper wafer $W_U$. Further, the pressing member 250 presses the central portion of the upper wafer $W_U$ and the central portion of the lower wafer $W_L$ in contact with each other (Operation S12 in FIG. 25).

Thus, bonding between the pressed central portions of the upper and lower wafers $W_U$ and $W_L$ begins (see a thick line indicated in FIG. 28). Specifically, since the front surface $W_{U1}$ of the upper wafer $W_U$ and the front surface $W_{L1}$ of the lower wafer $W_L$ have been modified in Operations S1 and S6, respectively, the Van der Waals force (inter-molecular force) is caused between the front surfaces $W_{U1}$ and $W_{L1}$ so that the front surfaces $W_{U1}$ and $W_{L1}$ are bonded together. In addition, since the front surface $W_{U1}$ of the upper wafer $W_U$ and the front surface $W_{L1}$ of the lower wafer $W_L$ have been hydrophilized in Operations S2 and S7, respectively, hydrophilic groups between the front surfaces $W_{U1}$ and $W_{L1}$ form a hydrogen-bonding (inter-molecular force), which provides a strong bonding between the front surfaces $W_{U1}$ and $W_{L1}$.

Figure 29:
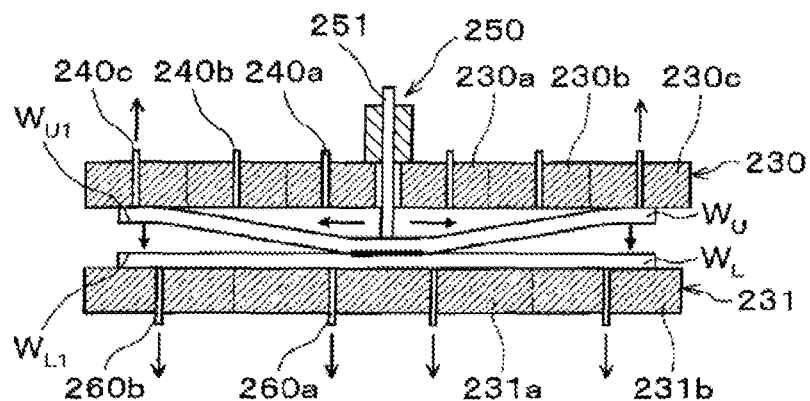
FIG. 29 is an explanatory view showing how to gradually bring the upper wafer and the lower wafer into contact with each other.
Figure 30:
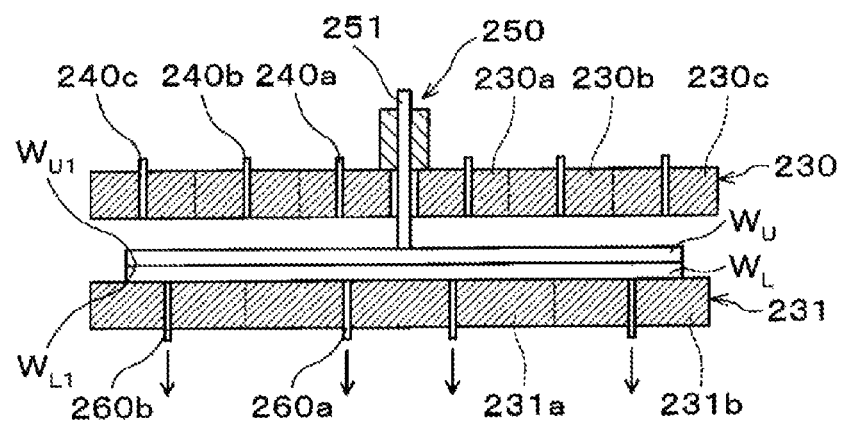
FIG. 30 is an explanatory view showing how to bring surfaces of the upper wafer and the lower wafer into contact with each other.

Thereafter, as shown in FIG. 29, in a state where the central portions of the upper and lower wafers $W_U$ and $W_L$ are pressed by the pressing member 250, the second vacuum pump 241b is deactivated to stop the suction of the upper wafer $W_U$ by the second suction pipe 240b in the second region 230b. This allows the upper wafer $W_U$ adsorbed in the second region 230b to be dropped on the lower wafer $W_L$. Subsequently, the third vacuum pump 241c is deactivated to stop the suction of the upper wafer $W_U$ by the third suction pipe 240c in the third region 230c. In this way, the suction of the upper wafer $W_U$ is gradually stopped from the central portion to the periphery of the upper wafer $W_U$ so that the upper wafer $W_U$ is gradually dropped on the lower wafer $W_L$, which makes the upper wafer $W_U$ and the lower wafer $W_L$ to be brought into contact with each other. Further, the Van der Waals force between the front surfaces $W_{U1}$ and $W_{L1}$ and the bonding according to the hydrogen bonding therebetween are gradually expanded. Thus, as shown in FIG. 30, the front surface $W_{U1}$ of the upper wafer $W_U$ and the front surface $W_{L1}$ of the lower wafer $W_L$ are brought into contact with each other in whole so that the upper wafer $W_U$ and the lower wafer $W_L$ are bonded (Operation S13 in FIG. 25).

Figure 31:
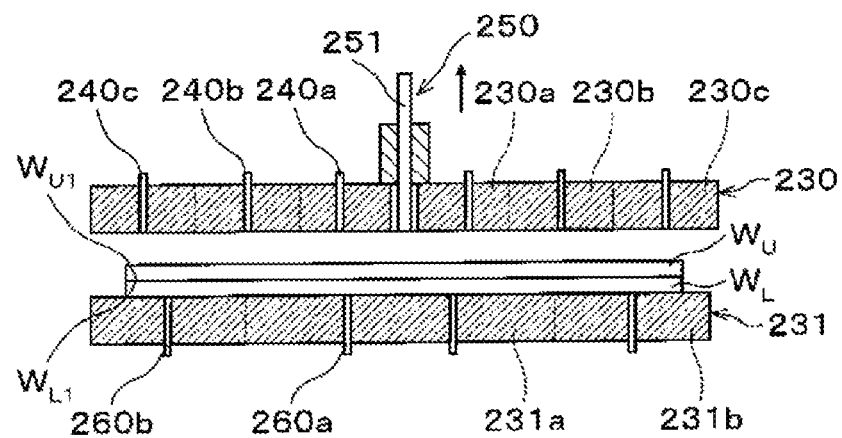
FIG. 31 is an explanatory view showing a state where the upper wafer and the lower wafer are bonded together.

Thereafter, as shown in FIG. 31, the pressing member 250 is ascended up to the upper chuck 230. In addition, the suction of the lower wafer $W_L$ by the lower chuck 231 through the suction pipes 260a and 260b is stopped such that the adsorption of the lower wafer $W_L$ by the lower chuck 231 is stopped.

Figure 32:
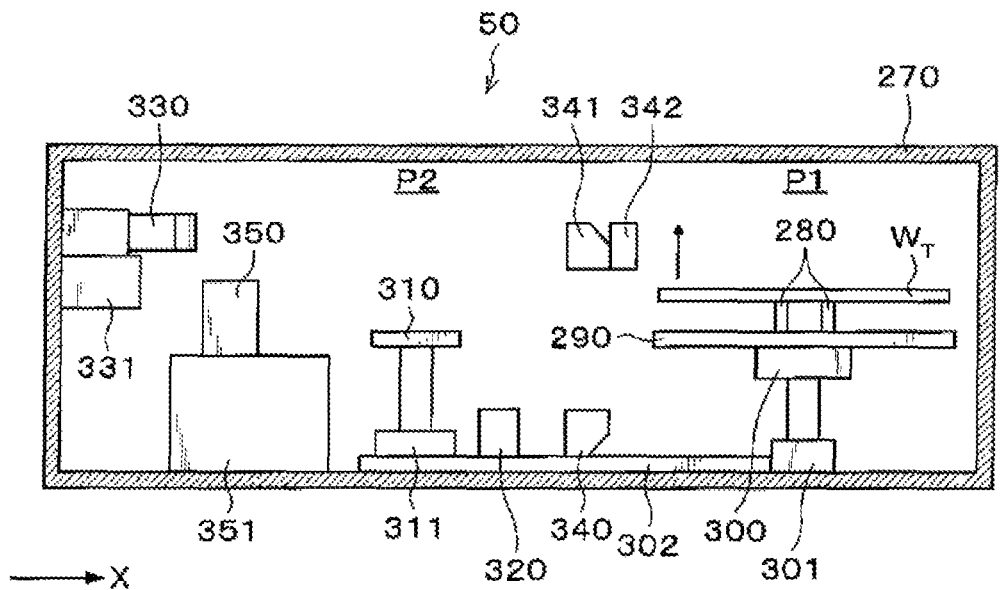
FIG. 32 is an explanatory view showing a state where an overlapped wafer is transferred from a wafer transfer unit to elevating pins.
Figure 33:
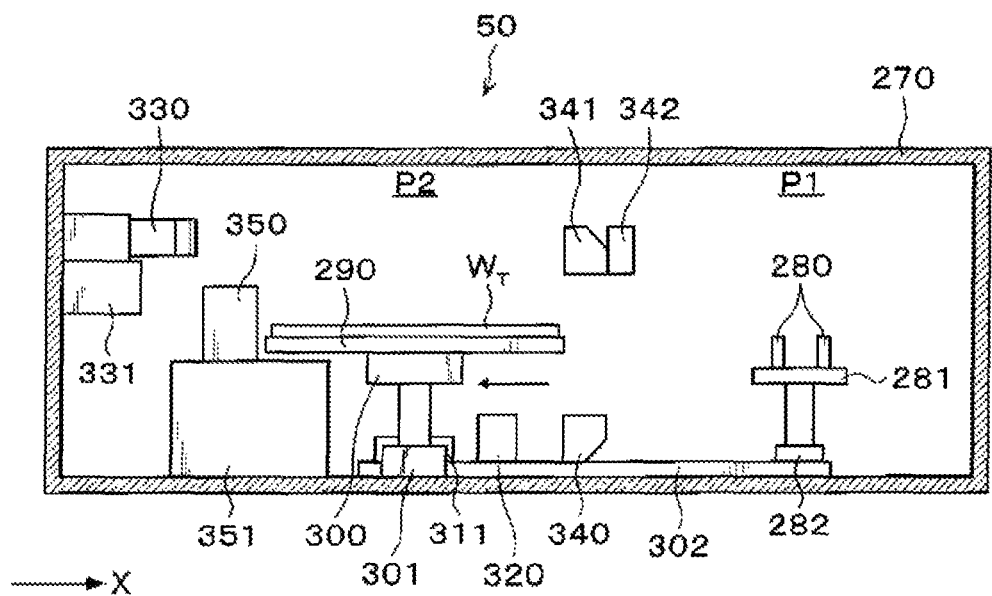
FIG. 33 is an explanatory view showing a state where a first holding unit is moved from a transfer sector to an inspection sector.

Subsequently, the overlapped wafer $W_T$ obtained by bonding the upper wafer $W_U$ and the lower wafer $W_L$ is transferred to the inspection device 50 by the wafer transfer unit 61 through the inlet/outlet 271. As shown in FIG. 32, in the inspection device 50, the overlapped wafer $W_T$ is transferred from the wafer transfer unit 61 on the elevating pins 280 ascended up to a predetermined height in advance. At this time, the first holding unit 290 waits below the elevating pins 280 in the transfer sector P1. Thereafter, the elevating pins 280 are moved downward so that the overlapped wafer $W_T$ is transferred from the elevating pins 280 on the first holding unit 290. Subsequently, as shown in FIG. 33, the first holding unit 290 is moved from the transfer sector P1 to the inspection sector P2.

Figure 34:
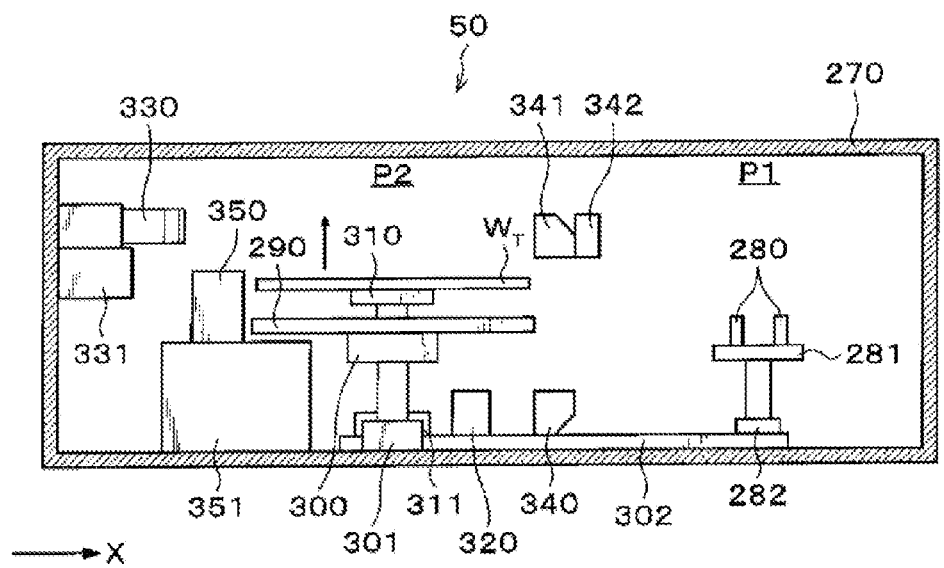
FIG. 34 is an explanatory view showing a state where the overlapped wafer is transferred from the first holding unit to a second holding unit.

After the first holding unit 290 is moved to the inspection sector P2, the second holding unit 310 is moved upward as shown in FIG. 34 so that the overlapped wafer $W_T$ is transferred from the first holding unit 290 to the second holding unit 310.

Thereafter, the displacement gauge 350 irradiates a laser beam toward peripheral sides of the upper wafer $W_U$ and the lower wafer $W_L$ of the overlapped wafer $W_T$ while rotating the second holding unit 310. The displacement gauge 350 receives the laser beam reflected at each of the peripheral sides of the upper wafer $W_U$ and the lower wafer $W_L$ and measures displacements of the peripheral sides of the upper wafer $W_U$ and the lower wafer $W_L$. The overlapped wafer $W_T$ is rotated by the second holding unit 310 at least one or more times. By doing so, the displacements of the entire peripheral sides of the upper wafer $W_U$ and the lower wafer $W_L$ are measured so that a misalignment between the upper wafer $W_U$ and the lower wafer $W_L$ (a bonding state of the overlapped wafer $W_T$) is inspected (Operation S14 in FIG. 25).

Thereafter, positions of the notch portions are detected at the position detecting mechanism 351 while rotating the second holding unit 310. Then, the overlapped wafer $W_T$ is arranged at a specified position by adjusting the positions of the notch portions of the overlapped wafer $W_T$ (Operation S15 in FIG. 25).

Upon adjusting the positions of the notch portions of the overlapped wafer $W_T$, the second holding unit 310 is moved downward so that the overlapped wafer $W_T$ is transferred from the second holding unit 310 to the first holding unit 290.

Figure 35:
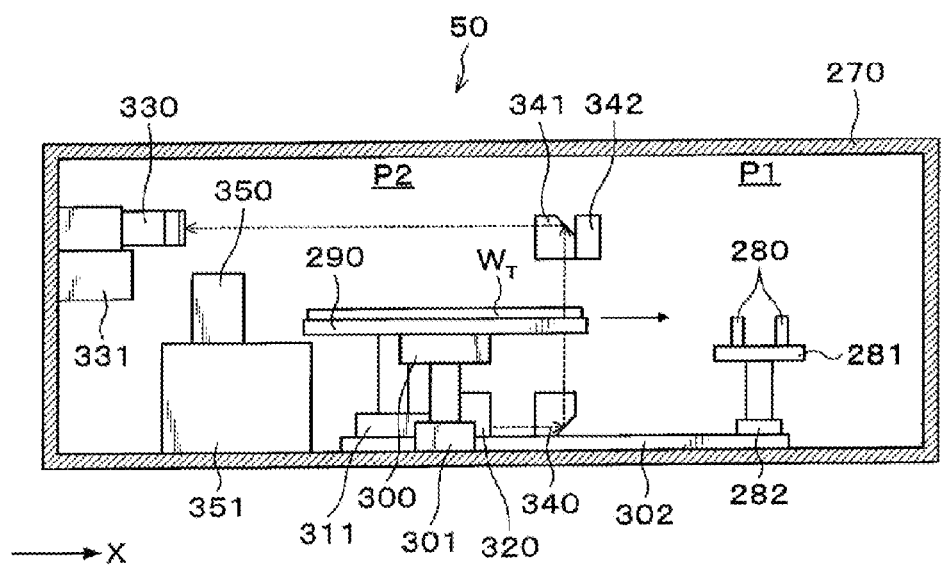
FIG. 35 is an explanatory view showing a state where the overlapped wafer is picked up by moving the first holding unit.
Figure 36:
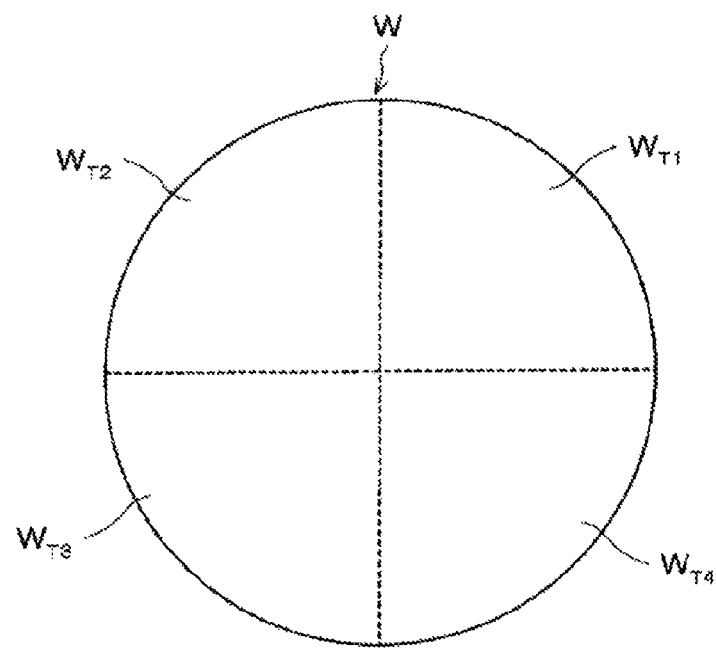
FIG. 36 is an explanatory view showing divided portions of the overlapped wafer.

Thereafter, as shown in FIG. 35, while the infrared irradiation unit 320 irradiates the infrared ray toward the first direction changing unit 340, the first holding unit 290 is moved from the inspection sector P2 toward the transfer sector P1. When the overlapped wafer $W_T$ held by the first holding unit 290 is transferred to pass by the first direction changing unit 340, the infrared ray reflected at the first direction changing unit 340 transmit an exposed portion of the overlapped wafer $W_T$ through the cutout 295. Then, the infrared ray transmitted through the exposed portion is reflected at the second direction changing unit 341 and is directed into the image pickup unit 330. The first holding unit 290 is moved up to a position where the irradiation of the infrared ray onto the first exposed portion $W_{T1}$ of the overlapped wafer $W_T$ (see FIG. 36) through the cutout 295 is ended, i.e., up to a side surface of the second support member 292 in the vicinity of the transfer sector P 1. Thus, as shown in FIG. 36, an image of the first exposed portion $W_{T1}$ of the overlapped wafer $W_T$ through the cutout 295, i.e., a ¼ of the overlapped wafer $W_T$, is picked up by the image pickup unit 330 (Operation S16 in FIG. 25).

In Operation S16 of this embodiment, a scheme, namely, a line sensor scheme, of picking up the overlapped wafer $W_T$ while moving the same is used. In case of using, e.g., an area sensor scheme of picking up the entirety of the overlapped wafer $W_T$ at one time, the number of pixels of a picked-up image is too small, which makes it difficult to inspect the interior of the overlapped wafer $W_T$.

After the overlapped wafer $W_{T1}$ is picked up by the image pickup unit 330, the first holding unit 290 is moved to the inspection sector P2 again. Subsequently, in an analogous manner as shown in FIG. 34, the second holding unit 310 is moved up so that the overlapped wafer $W_T$ is transferred from the first holding unit 290 to the second holding unit 310. Thereafter, the second holding unit 310 is rotated by 90 degrees such that a second portion $W_{T2}$ of the overlapped wafer $W_T$ as shown in FIG. 36 is exposed through the cutout 295 (Operation S17 in FIG. 25).

Subsequently, the second holding unit 310 is moved downward so that the overlapped wafer $W_T$ is transferred from the second holding unit 310 to the first holding unit 290. Thereafter, by doing Operation S16 as described above, the second exposed portion $W_{T2}$ of the overlapped wafer $W_T$ as shown in FIG. 36 is picked up by the image pickup unit 330.

Subsequently, by repeatedly performing Operations S16 and S17, the remaining portions of the overlapped wafer $W_T$, i.e., a third exposed portion $W_{T3}$ and a fourth exposed portion $W_{T4}$ as shown in FIG. 36, are picked up by the image pickup unit 330. The images of the first to fourth portions $W_{T1}$ to $W_{T4}$, which are picked divisionally up four times in this manner, are outputted from the image pickup unit 330 to the controller 400. The controller 400 combines the picked-up images of the first to fourth exposed portions $W_{T1}$ to $W_{T4}$ to obtain a whole image of the overlapped wafer $W_T$. Based on the whole image of the overlapped wafer $W_T$, an inspection operation is performed to check whether or not voids exist in the interior of the overlapped wafer $W_T$ (Operation S18 in FIG. 25).

Upon completing the inspection operation on the interior of the overlapped wafer $W_T$, the first holding unit 290 holding the overlapped wafer $W_T$ is moved to the transfer sector P1. Subsequently, the overlapped wafer $W_T$ is transferred from the first holding unit 290 on the elevating pins 280. Thereafter, the overlapped wafer $W_T$ is conveyed from the elevating pins 280 to the wafer transfer unit 22 and subsequently, is unloaded from the inspection device 50 through the inlet/outlet 273.

Thereafter, the overlapped wafer $W_T$ is transferred to the cassette $C_T$ loaded on the specified cassette loading board 11 by the wafer transfer unit 22. In this way, a series of bonding process of the wafers $W_U$ and $W_L$ is completed.

With the above embodiments, the displacement gauge 350 is installed within the inspection device 50 and measures each of the displacements of the peripheral sides of the upper wafer $W_U$ and the lower wafer $W_L$ of the overlapped wafer $W_T$ while rotating the overlapped wafer $W_T$ held by the second holding unit 310 (Operation S14), thereby stably inspecting the bonding state of the overlapped wafer $W_T$. Further, since the bonding state of the overlapped wafer $W_T$ is inspected by only the second holding unit 310 and the displacement gauge 350, there is no need to use a large-scale mechanism, which miniaturizes the inspection device 50.

As described above, the first holding unit 290 of the inspection device 50 includes the cutout 295 formed therein. In the related art, the infrared ray is impossible to transmit through a holding unit which holds an overlapped wafer, which fails to pick up the overlapped wafer held by the holding unit. In this embodiment, however, the cutout 295 is formed in the first holding unit 290, which makes it possible to pick divisionally up a quarter of the overlapped wafer $W_T$ while holding the overlapped wafer $W_T$ by the first holding unit 290 in Operation S16. Further, the whole image of the overlapped wafer $W_T$ can be stably picked up by repeatedly performing the aforementioned Operation S16 and Operation S17 of rotating the overlapped wafer $W_T$ using the second holding unit 310. Accordingly, based on the whole image of the overlapped wafer $W_T$, it is possible to properly inspect the interior of the overlapped wafer $W_T$.

Further, since both the inspection operations of the bonding state of the overlapped wafer $W_T$ and the interior of the overlapped wafer $W_T$ can be performed within the single inspection device 50 as described above, it is possible to efficiently inspect the overlapped wafer $W_T$. Further, this simplifies the configuration of the bonding system 1.

As described above, the first holding unit 290 is provided with the four support members 291 to 294 which are arranged to be orthogonal to each other when viewed from the top, which makes it possible to properly form the cutout 295 to expose a quarter of the rear surface of the overlapped wafer $W_T$ therethrough. This makes it possible to pick divisionally up the quarter image of the overlapped wafer $W_T$ in Operation S16. The present inventors have examined this discovery and have found that, in order for the controller 400 to easily combine the divisionally picked-up images of the overlapped wafer $W_T$, it is desirable to pick up the overlapped wafer $W_T$ by dividing the overlapped wafer $W_T$ into four portions as described in this embodiment.

In this embodiment, a wavelength of the infrared ray irradiated from the infrared irradiation unit 320 falls within a range of 1,100 nm to 2,000 nm, which makes it possible to transmit the infrared ray through the overlapped wafer $W_T$. Further, the infrared ray irradiated from the infrared irradiation unit 320 is collected by the cylindrical lens 345 and subsequently, is uniformly diffused in plane of the overlapped wafer $W_T$ by the diffusion plate 346. It is therefore possible to stably pick up the image of the overlapped wafer $W_T$ in Operation S16.

As described above, in addition to the inspection device 50, the bonding system 1 further includes the surface modification device 30, the surface hydrophilization device 40 and the bonding device 41 which are used in bonding the wafers $W_U$ and $W_L$ together, which makes it possible to efficiently perform the bonding operation of the wafers $W_U$ and $W_L$ and the inspection operation on the interior of the overlapped wafer $W_T$ in only the bonding system 1. Accordingly, it is possible to further improve a production yield in the wafer bonding process.

Figure 37:
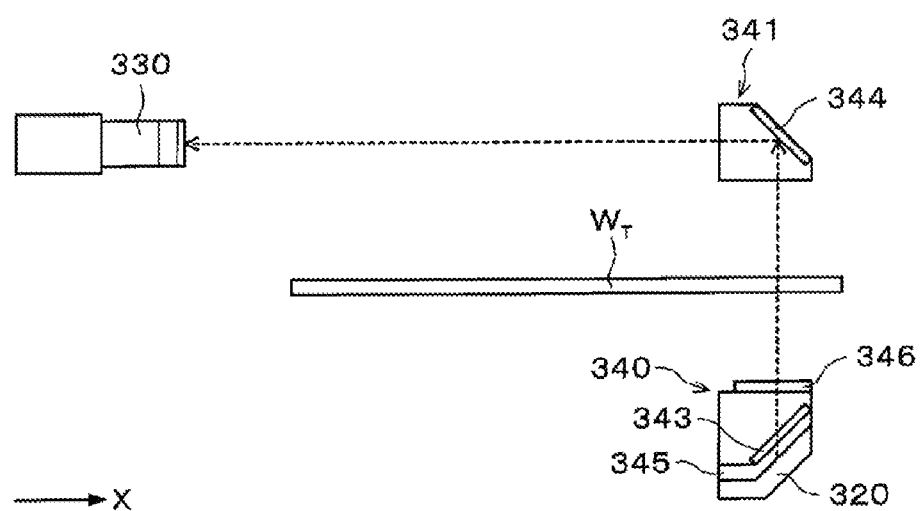
FIG. 37 is an explanatory view showing a path of an infrared ray traveling between an infrared irradiation unit and an image pickup unit according to some embodiments.

While in the above embodiment, the infrared irradiation unit 320 has been described to be installed at the side of the first direction changing unit 340 in the inspection sector P2, as shown in FIG. 37, the infrared irradiation unit 320 may be integrated with the first direction changing unit 340 on the lower side of the first direction changing unit 340. Further, in some embodiments, the cylindrical lens 345 may be installed between the infrared irradiation unit 320 and the first reflection mirror 343. Further, a half mirror may be employed as an example of the first reflection mirror 343. In this embodiment, the first reflection mirror 343 may be omitted.

Further, the infrared ray irradiated from the infrared irradiation unit 320 transmits through the overlapped wafer $W_T$ via a series of the cylindrical lens 345, the first reflection mirror 343 and the diffusion plate 346 and subsequently, is directed to the image pickup unit 330 via the second reflection mirror 344. With this configuration, similarly to the above embodiments, it is possible to pick divisionally up the image of the overlapped wafer $W_T$ in Operation S16 and stably inspect the interior of the overlapped wafer $W_T$ based on the whole image obtained by combining the divisionally picked-up images of the overlapped wafer $W_T$.

Figure 38:
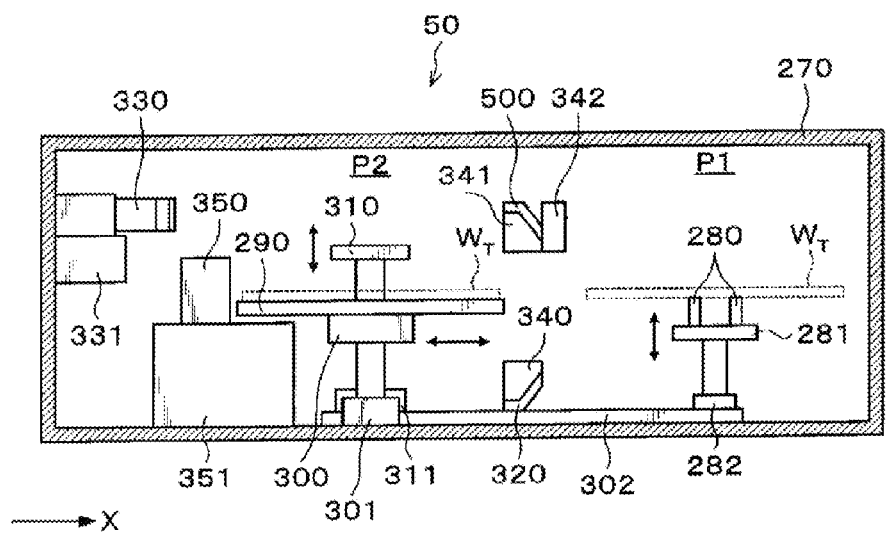
FIG. 38 is a longitudinal sectional view schematically showing a configuration of an inspection device according to some embodiments.

In some embodiments, as shown in FIG. 38, the inspection device 50 may include an additional infrared irradiation unit 500 configured to irradiate an infrared ray onto the front surface of the overlapped wafer $W_T$ held by the first holding unit 290. As shown in FIG. 38, the additional infrared irradiation unit 500 may be integrated with the second direction changing unit 341 on the upper surface of the second direction changing unit 341. A cylindrical lens 501 configured to collect the infrared ray to be irradiated onto the overlapped wafer $W_T$ is installed between the additional infrared irradiation unit 500 and the second reflection mirror 344. A diffusion plate 502, which is configured to uniformly diffuse the infrared ray transmitting through the cylindrical lens 501 in plane of the overlapped wafer $W_T$, is installed on the lower side of the second direction changing unit 341. Examples of the second reflection mirror 344 may include a half mirror.

Figure 40:
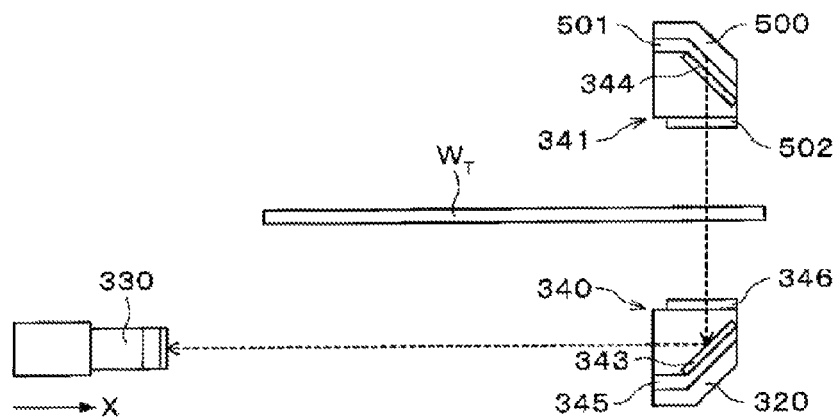
FIG. 40 is an explanatory view showing a path of an infrared ray traveling between an infrared irradiation unit and an image pickup unit according to some embodiments.

The second direction changing unit 341, the second reflection mirror 344, the additional infrared irradiation unit 500, the cylindrical lens 501 and the diffusion plate 502 are identical in configuration with the first direction changing unit 340, the first reflection mirror 343, the infrared irradiation unit 320, the cylindrical lens 345 and the diffusion plate 346 of the aforementioned embodiment, and these components are arranged opposite to each other with the overlapped wafer $W_T$ interposed therebetween, as shown in FIG. 40.

The support member 331 configured to support the image pickup unit 330 as shown in FIG. 38 includes an elevating mechanism (not shown) configured to vertically move the image pickup unit 330.

Figure 39:
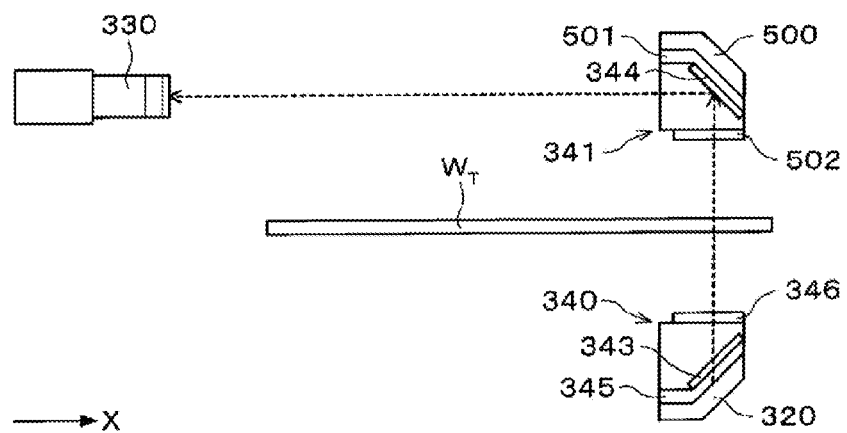
FIG. 39 is an explanatory view showing a path of an infrared ray traveling between an infrared irradiation unit and an image pickup unit according to some embodiments.

With this configuration, when the infrared ray are irradiated from the infrared irradiation unit 320 via the rear surface of the overlapped wafer $W_T$, the image pickup unit 330 is moved up to the vicinity of the upper surface of the overlapped wafer $W_T$ as shown in FIG. 39. Subsequently, the infrared ray irradiated from the infrared irradiation unit 320 transmits through the overlapped wafer $W_T$ after transferred through the cylindrical lens 345, the first reflection mirror 343 and the diffusion plate 346 and subsequently, is directed to the image pickup unit 330 via the second reflection mirror 344. In this way, the image of the overlapped wafer $W_T$ is picked divisionally up.

On the other hand, when the infrared ray is irradiated from the additional infrared irradiation unit 500 via the front surface of the overlapped wafer $W_T$, as shown in FIG. 40, the image pickup unit 330 is moved up to in the vicinity of the lower surface of the overlapped wafer $W_T$. Then, the infrared ray irradiated from the additional infrared irradiation unit 500 transmits through the overlapped wafer $W_T$ after transferred through the cylindrical lens 501, the second reflection mirror 344 and the diffusion plate 502 and subsequently, is directed to the image pickup unit 330 via the first reflection mirror 343. Thus, the image of the overlapped wafer $W_T$ is picked divisionally up.

According to the above embodiments, it is possible to selectively irradiate the infrared ray through the rear surface of the overlapped wafer $W_T$ using the infrared irradiation unit 320 or the front surface of the overlapped wafer $W_T$ using the additional infrared irradiation unit 500. With this configuration, it is possible to stably pick up the overlapped wafer $W_T$ and to stably inspect the interior of the overlapped wafer $W_T$, regardless of the state of the overlapped wafer $W_T$ to be transferred to the inspection device 50. For example, even when the inspection operation is performed through a specific surface of the overlapped wafer $W_T$, it is possible to freely pick up the image of the overlapped wafer $W_T$ without having to invert the front and rear surfaces of the overlapped wafer $W_T$.

While in the above embodiment, the cutout 295 of the first holding unit 290 has been described to be formed to expose the quarter of the rear surface of the overlapped wafer $W_T$ therethrough, the present disclosure is not limited thereto. As an example, the cutout 295 of the first holding unit 290 may be formed to expose one half, one third or one eighth of the rear surface of the overlapped wafer $W_T$. In any case, the image of the overlapped wafer $W_T$ can be picked divisionally up by the image pickup unit 330, which makes it possible to pick up exposed portions of the overlapped wafer $W_T$ held by the holding unit. This makes it possible to stably pick up the whole image of the overlapped wafer $W_T$.

While in the above embodiment, the inspection device 50 equipped with the displacement gauge 350 has been described to inspect the interior of the overlapped wafer $W_T$ by irradiating the infrared ray onto the overlapped wafer $W_T$, the present disclosure is not limited thereto. As an example, light may be irradiated onto the front surface of the overlapped wafer $W_T$ to inspect the interior of the overlapped wafer $W_T$.

Figure 41:
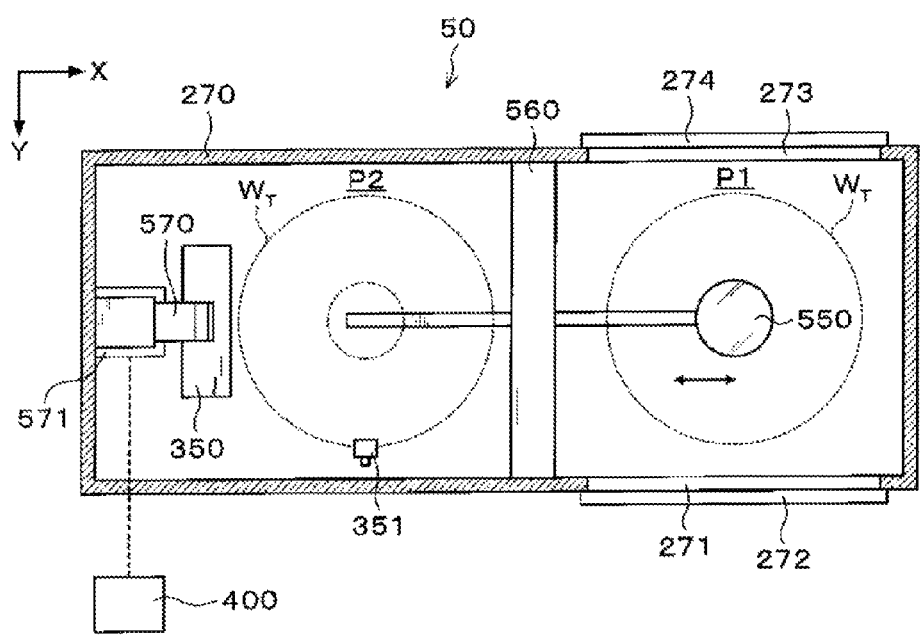
FIG. 41 is a traverse sectional view schematically showing a configuration of an inspection device according to some embodiments.
Figure 42:
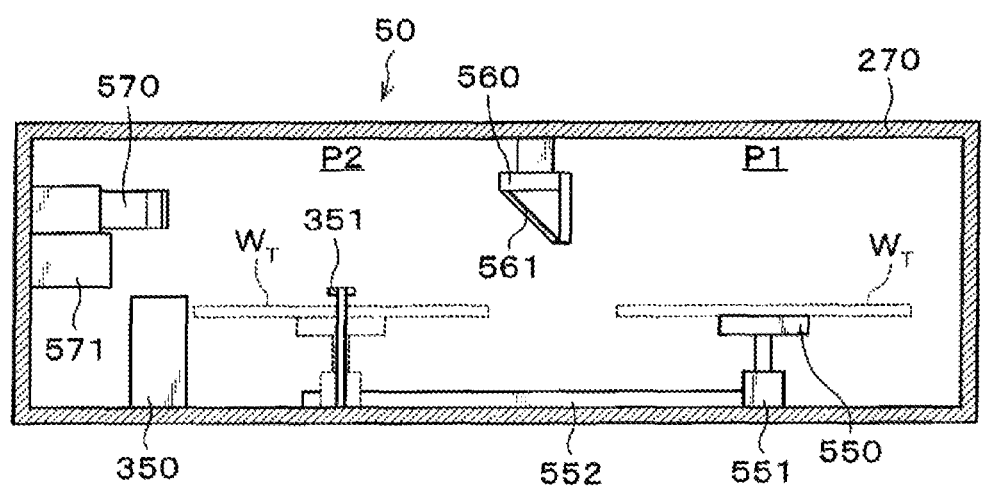
FIG. 42 is a longitudinal sectional view schematically showing a configuration of an inspection device according to some embodiments.

As shown in FIGS. 41 and 42, a holding unit 550 configured to adsorb the overlapped wafer $W_T$ is installed within the processing vessel 270 of the inspection device 50. The holding unit 550 includes a horizontal upper surface on which suction holes (not shown) for suctioning the overlapped wafer $W_T$ is formed. By virtue of the suctioning force of the suction holes, the overlapped wafer $W_T$ can be adsorbed to the holding unit 550.

As shown in FIG. 42, the holding unit 550 is connected to a drive unit 551. The drive unit 551 is equipped with, e.g., a motor (not shown). The drive unit 551 can rotate the holding unit 550 and can adjust a position of the overlapped wafer $W_T$. A rail 552 extending in the X-axis direction in FIGS. 41 and 42 is installed on a bottom surface of the processing vessel 270. The drive unit 551 is attached to the rail 552. The holding unit 550 (or the drive unit 551) is configured to move along the rail 552 between the transfer sector P1 where the overlapped wafer $W_T$ is transferred between the inspection device 50 and the outside, and the inspection sector P2 where the bonding state of the overlapped wafer $W_T$ is inspected by the displacement gauge 350. The holding unit 550 is movable up and down by the operation of the drive unit 551.

A lighting unit 560, which is configured to irradiate light onto the front surface of the overlapped wafer $W_T$ held by the holding unit 550, is installed inside the processing vessel 270. The lighting unit 560 is disposed above the holding unit 550 between the transfer sector P1 and the inspection sector P2. The lighting unit 560 extends in the Y-axis direction. A half mirror 561 is installed underneath the lighting unit 560. The half mirror 561 is installed to face an image pickup unit 570 (which will be described later) and is inclined by 45 degrees with respect to a vertical axis.

An image pickup unit 570, which is configured to receive the light irradiated from the lighting unit 560 and pick up an image of the front surface of the overlapped wafer $W_T$ held by the holding unit 550, is installed inside the processing vessel 270. Examples of the image pickup unit 570 may include a wide-angle CCD camera. The image pickup unit 570 is disposed at the backside of the inspection sector P2 in the X-axis direction, i.e., at the backside of the processing vessel 270 in the X-axis direction and above the holding unit 550. The image pickup unit 570 is supported by the support member 571. The image pickup unit 570 is connected to the controller 400. A picked-up image of the overlapped wafer $W_T$ by the image pickup unit 570 is outputted to the controller 400.

The aforementioned displacement gauge 350 configured to measure the displacement of the peripheral side of the overlapped wafer $W_T$ held by the second holding unit 310 is installed inside the processing vessel 270. The displacement gauge 350 is installed at the backside of the inspection sector P2 in the X-axis direction.

The aforementioned position detecting mechanism 351 configured to detect the position of the overlapped wafer $W_T$ held by the second holding unit 310 is installed in the inspection sector P2 within the processing vessel 270. The position detecting mechanism 351 is equipped with, e.g., a CCD camera (not shown), and is configured to detect the positions of the notch portions formed in the overlapped wafer $W_T$ held by the second holding unit 310.

In this configuration, the overlapped wafer $W_T$ transferred to the inspection device 50 is transferred from the wafer transfer unit 61 to the holding unit 550. Thereafter, the holding unit 550 is moved from the transfer sector P1 to the inspection sector P2.

Thereafter, in Operation S14, the displacement gauge 350 irradiates a laser beam onto the peripheral sides of the upper wafer $W_U$ and the lower wafer $W_L$ of the overlapped wafer $W_T$ while rotating the holding unit 550. The displacement gauge 350 receives the laser beam reflected from the peripheral sides of the upper wafer $W_U$ and the lower wafer $W_L$ and detects displacements of the peripheral sides of the upper wafer $W_U$ and the lower wafer $W_L$. The overlapped wafer $W_T$ is rotated by the holding unit 550 at least one times. Thus, the displacements of the entire peripheral sides of the upper wafer $W_U$ and the lower wafer $W_L$ are measured so that a misalignment between the upper wafer $W_U$ and the lower wafer $W_L$ (a bonding state of the overlapped wafer $W_T$) is inspected.

Thereafter, in Operation S15, the position detecting mechanism 351 detects the positions of the notch portions while rotating the second holding unit 310. Then, the positions of the notch portions of the overlapped wafer $W_T$ are adjusted such that the overlapped wafer $W_T$ is arranged at a specified position.

Subsequently, while the holding unit 550 is moved from the inspection sector P2 toward the transfer sector P1, light is irradiated from the lighting unit 560 onto the overlapped wafer $W_T$ under movement. The irradiated light is reflected at the front surface of the overlapped wafer $W_T$ and is directed into the image pickup unit 570 via the half mirror 561. Based on the irradiated light, the image pickup unit 570 picks up an image of the front surface of the overlapped wafer $W_T$. The picked-up image of the overlapped wafer $W_T$ is outputted to the controller 400 where an inspection is performed to whether a defect exists in the front surface of the overlapped wafer $W_T$. Thereafter, the holding unit 550 holding the overlapped wafer $W_T$ is moved to the transfer sector P1. Subsequently, the overlapped wafer $W_T$ is conveyed from the holding unit 550 to the wafer transfer unit 22 and is unloaded from the inspection device 50 through the inlet/outlet 273.

In this embodiment, the displacements of the peripheral sides of the upper wafer $W_U$ and the lower wafer $W_L$ of the overlapped wafer $W_T$ can be measured in Operation S14 by the displacement gauge 350 while rotating the overlapped wafer $W_T$ held by the second holding unit 310, thereby stably inspecting the bonding state of the overlapped wafer $W_T$. Both operations of inspecting the bonding state of the overlapped wafer $W_T$ and the front surface of the overlapped wafer $W_T$ are performed within the single inspection device 50, which makes it possible to efficiently inspect the overlapped wafer $W_T$.

While in the above embodiment, the interior of the overlapped wafer $W_T$ obtained by bonding the wafers $W_U$ and $W_L$ by virtue of the Van der Waals force and the hydrogen bond has been described to be inspected, the present disclosure is not limited thereto. For example, the present disclosure may be applied to an overlapped wafers $W_T$ bonded by another methods.

For example, a wafer to be processed having an increased diameter and a reduced thickness is often used in the up-to-date semiconductor manufacturing process. When the wafer to be processed is directly transferred or subjected to a polishing process, it is likely that a warp or a crack is generated in the wafer to be processed. As such, in order to reinforce the wafer to be processed, a support wafer is bonded to the wafer to be processed using, e.g., an adhesive. The wafer to be processed is used as a product. For example, a plurality of electronic circuits is formed on a bonding surface of the wafer to be processed and the support wafer.

The bonding state of the overlapped wafer $W_T$ obtained by bonding the wafer to be processed and the support wafer can be inspected by the inspection device 50. Further, the inspection device 50 can inspect the interior of the overlapped wafer $W_T$ and the front surface of the overlapped wafer $W_T$.

When bonding two wafers, metal portions attached to the surfaces of the wafers are sometimes bonded together. A bonding state of the overlapped wafer $W_T$ bonded in this manner can be also inspected by the inspection device 50.

In the above embodiment, the inspection device 50 has been described to inspect the bonding state of the overlapped wafer $W_T$ and the interior of the overlapped wafer $W_T$ or the front surface of the overlapped wafer $W_T$, but may inspect only the bonding state of the overlapped wafer $W_T$.

While in the bonding device 41 of the above embodiment, the chuck drive unit 234 has been described to move the lower chuck 231 in both the vertical and horizontal directions, the present disclosure is not limited thereto. In some embodiments, the upper chuck 230 may be configured to move in any one of the vertical and horizontal directions. Alternatively, both the upper chuck 230 and the lower chuck 231 may be configured to move the vertical and horizontal directions.

While in FIG. 40, the additional infrared irradiation unit 500 has been described to irradiate the infrared ray onto the front surface of the overlapped wafer $W_T$, the present disclosure is not limited thereto. As an example, as shown in FIG. 39, by reversing the arrangement shown in FIG. 40 upside down, the infrared irradiation unit 320 may be disposed in the vicinity of the rear surface of the overlapped wafer $W_T$ such that the infrared ray is irradiated onto the rear surface of the overlapped wafer $W_T$.

According to the present disclosure, it is possible to miniaturize an inspection device which inspects an overlapped substrate obtained by bonding substrates together and to stably inspect a bonding state of the overlapped substrate using the inspection device.

While certain embodiments have been described, these embodiments have been presented by way of example only, and are not intended to limit the scope of the disclosures. Indeed, the novel methods and apparatuses described herein may be embodied in a variety of other forms. Furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures. The present disclosure may be applied to other various substrates including a metal substrate, a flat panel display (FPD), a mask reticle for a photomask and so on.

What is claimed is:

1. An apparatus of inspecting an overlapped substrate obtained by bonding substrates together, comprising:
    a first holding unit configured to hold and rotate the overlapped substrate;
    a displacement gauge configured to measure displacements of peripheral sides of a first substrate and a second substrate constituting the overlapped substrate while rotating the overlapped substrate held by the first holding unit;
    a second holding unit configured to hold a rear surface of the overlapped substrate, and including a cutout to expose a portion of the rear surface of the overlapped substrate therethrough when viewed from the top;
    a first infrared irradiation unit configured to irradiate an infrared ray on the exposed portion of the rear surface or a front surface of the overlapped substrate which is exposed through the cutout of the second holding unit; and
    an image pickup unit configured to receive the infrared ray irradiated from the first infrared irradiation unit and configured to pick up images of the exposed portions of the rear surface or the front surface of the overlapped substrate, which are exposed through the cutout of the second holding unit,
    wherein the cutout is formed to expose a quarter of the rear surface of the overlapped substrate therethrough,
    wherein the second holding unit includes four support members configured to hold the rear surface of the overlapped substrate, and wherein the four support members are formed to be orthogonal to each other when viewed from the top.

2. The apparatus of claim 1, further comprising:
a second infrared irradiation unit configured to irradiate an infrared ray onto the front surface or the rear surface of the overlapped substrate held by the second holding unit.

3. A method of inspecting an overlapped substrate obtained by bonding substrates together using the inspection device according to claim 2, comprising:
measuring, by the displacement gauge, displacements of peripheral sides of first and second substrates constituting the overlapped substrate while rotating the overlapped substrate held by the first holding unit;
inspecting a bonding state of the overlapped substrate;
selectively irradiating, by the first infrared irradiation unit, the infrared ray onto the exposed portion of the rear surface or the front surface of the overlapped substrate through the cutout, or irradiating, by the second infrared irradiation unit, the infrared ray onto the front surface or the rear surface of the overlapped substrate;
receiving, by the image pickup unit, the infrared ray irradiated from the first infrared irradiation unit and picking up the image of the exposed portion of the overlapped substrate through the cutout;
rotating, by the first holding unit, the overlapped substrate such that other portions of the rear surface of the overlapped substrate, which are not picked up in the picking up, are exposed through the cutout, in a state where the overlapped substrate is held by the first holding unit;
imaging an entire image of the overlapped substrate by repeatedly performing a sequence of the picking up and the rotating predetermined times; and
inspecting the interior of the overlapped substrate.

4. The apparatus of claim 1, wherein a wavelength of the infrared ray falls within a range of 1,100 nm to 2,000 nm.

5. A bonding system including the inspection device of claim 1, comprising:
a processing station including a plurality of processing units configured to perform a predetermined process to bond substrates together, and a substrate transfer zone in which first and second substrates before the bonding or an overlapped substrate after the bonding are transferred to the plurality of processing units; and
a carry-in/carry-out station in which the first and second substrates before the bonding or the overlapped substrate after the bonding are carried in and out the processing station,
wherein the inspection device is disposed adjacent to the substrate transfer zone and the carry-in/carry-out station inside the processing station.

6. A method of inspecting an overlapped substrate obtained by bonding substrates together using the inspection device according to claim 3, comprising:
measuring, by the displacement gauge, displacements of peripheral sides of first and second substrates constituting the overlapped substrate while rotating the overlapped substrate held by the first holding unit;
inspecting a bonding state of the overlapped substrate;
irradiating, by the first infrared irradiation unit, the infrared ray onto the exposed portion of the rear surface or the front surface of the overlapped substrate through the cutout in a state where the overlapped substrate is held by the second holding unit;
receiving, by the image pickup unit, the infrared ray irradiated from the first infrared irradiation unit and picking up the image of the exposed portion of the overlapped substrate through the cutout;
rotating, by the first holding unit, the overlapped substrate such that other portions of the rear surface of the overlapped substrate, which are not picked up in the picking up, are exposed through the cutout, in a state where the overlapped substrate is held by the first holding unit;
imaging an entire image of the overlapped substrate by repeatedly performing a sequence of the picking up and the rotating predetermined times; and
inspecting the interior of the overlapped substrate,
wherein the predetermined times are four times.

7. The method of claim 6, wherein a wavelength of the infrared ray falls within a range of 1,100 nm to 2,000 nm.

8. An apparatus of inspecting an overlapped substrate obtained by bonding substrates together, comprising:
a first holding unit configured to hold and rotate the overlapped substrate; and
a displacement gauge configured to measure displacements of peripheral sides of a first substrate and a second substrate constituting the overlapped substrate while rotating the overlapped substrate held by the first holding unit,
a second holding unit configured to hold a rear surface of the overlapped substrate, and including a cutout to expose a portion of the rear surface of the overlapped substrate therethrough when viewed from the top,
a first infrared irradiation unit configured to irradiate an infrared ray on the exposed portion of the rear surface or a front surface of the overlapped substrate which is exposed through the cutout of the second holding unit, and
an image pickup unit configured to receive the infrared ray irradiated from the first infrared irradiation unit and configured to pick up images of the exposed portions of the rear surface or the front surface of the overlapped substrate, which are exposed through the cutout of the second holding unit,
wherein the first holding unit is configured to move upward so that the overlapped substrate is transferred from the second holding unit to the first holding unit, and
wherein the first holding unit is configured to move downward so that the overlapped substrate is transferred from the first holding unit to the second holding unit.

9. A method of inspecting an overlapped substrate obtained by bonding substrates together using the inspection device according to claim 8, comprising:
measuring, by the displacement gauge, displacements of peripheral sides of first and second substrates constituting the overlapped substrate while rotating the overlapped substrate held by the first holding unit;
inspecting a bonding state of the overlapped substrate;
irradiating, by the first infrared irradiation unit, the infrared ray onto the exposed portion of the rear surface or the front surface of the overlapped substrate through the cutout in a state where the overlapped substrate is held by the second holding unit;
receiving, by the image pickup unit, the infrared ray irradiated from the first infrared irradiation unit and picking up the image of the exposed portion of the overlapped substrate through the cutout;
transferring the overlapped substrate from the second holding unit to the first holding unit;
rotating, by the first holding unit, the overlapped substrate such that other portions of the rear surface of the overlapped substrate, which are not picked up in the picking up, are exposed through the cutout, in a state where the overlapped substrate is held by the first holding unit;

transferring the overlapped substrate from the first holding unit to the second holding unit;
imaging an entire image of the overlapped substrate by repeatedly performing a sequence of the picking up and the rotating predetermined times; and
inspecting the interior of the overlapped substrate.

* * * * *

UNITED STATES PATENT AND TRADEMARK OFFICE
CERTIFICATE OF CORRECTION

| | | |
|---|---|---|
| PATENT NO. | : 9,097,681 B2 | Page 1 of 1 |
| APPLICATION NO. | : 13/967896 | |
| DATED | : August 4, 2015 | |
| INVENTOR(S) | : Shinji Koga et al. | |

It is certified that error appears in the above-identified patent and that said Letters Patent is hereby corrected as shown below:

In the claims

Claim 6, Column 27, Line 53: Replace "claim 3" with --claim 1--

Signed and Sealed this
Fifteenth Day of March, 2016

Michelle K. Lee
*Director of the United States Patent and Trademark Office*